US011612440B2

(12) United States Patent
Coakley et al.

(10) Patent No.: US 11,612,440 B2
(45) Date of Patent: Mar. 28, 2023

(54) SURGICAL INSTRUMENT TRACKING DEVICES AND RELATED METHODS

(71) Applicant: NuVasive, Inc., San Diego, CA (US)

(72) Inventors: Brett Coakley, San Diego, CA (US); Shoun Matsuka, San Diego, CA (US); Guy Nimrodi, San Diego, CA (US); Michael Serra, San Diego, CA (US); Michael Barela, San Diego, CA (US); Megan Jeffords, San Diego, CA (US); Danielle Richterkessing, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 40 days.

(21) Appl. No.: 17/003,215

(22) Filed: Aug. 26, 2020

(65) Prior Publication Data
US 2021/0068903 A1    Mar. 11, 2021

Related U.S. Application Data

(60) Provisional application No. 62/905,321, filed on Sep. 24, 2019, provisional application No. 62/896,128, filed on Sep. 5, 2019.

(51) Int. Cl.
*A61B 34/20* (2016.01)
*A61B 90/00* (2016.01)

(52) U.S. Cl.
CPC ...... *A61B 34/20* (2016.02); *A61B 2034/2057* (2016.02); *A61B 2034/2072* (2016.02); *A61B 2090/397* (2016.02); *A61B 2090/3937* (2016.02); *A61B 2090/3983* (2016.02)

(58) Field of Classification Search
None
See application file for complete search history.

(56) References Cited

U.S. PATENT DOCUMENTS

| 4,945,914 | A | 8/1990 | Allen |
| 5,211,164 | A | 5/1993 | Allen |
| 5,383,454 | A | 1/1995 | Bucholz |
| 5,389,101 | A | 2/1995 | Heilbrun |
| 5,603,318 | A | 2/1997 | Heilbrun |
| 5,836,954 | A | 11/1998 | Heilbrun |
| 6,273,896 | B1 | 8/2001 | Franck |
| 6,609,022 | B2 | 8/2003 | Stefan |
| 6,640,128 | B2 | 10/2003 | Stefan |

(Continued)

FOREIGN PATENT DOCUMENTS

| AU | 2013204941 B2 | 10/2015 |
| DE | 10306793 A1 | 12/2003 |

(Continued)

OTHER PUBLICATIONS

Schlenzka et al., Computer Assisted Spine Surgery, Eur Spine J (2000) 9 (Suppl 1): S56-S64.

(Continued)

*Primary Examiner* — Kaitlin A Retallick
(74) *Attorney, Agent, or Firm* — Merchant & Gould P.C.

(57) ABSTRACT

The present disclosure includes systems for surgical navigation, the system comprising a tracking array attachable to a medical instrument, an image capturing device, and a navigation system that communicates with the image capturing device and generates tracking information of the medical device.

9 Claims, 33 Drawing Sheets

(56) References Cited

U.S. PATENT DOCUMENTS

| | | |
|---|---|---|
| 6,725,079 B2 | 4/2004 | Yuval |
| 6,772,002 B2 | 8/2004 | Schmidt |
| 6,873,867 B2 | 3/2005 | Stefan |
| 6,877,239 B2 | 4/2005 | Leitner |
| 7,139,418 B2 | 11/2006 | Abovitz |
| 7,233,820 B2 | 6/2007 | Gilboa |
| 7,542,791 B2 | 6/2009 | Mire |
| 7,561,733 B2 | 7/2009 | Stefan |
| 7,567,834 B2 | 7/2009 | Clayton |
| 7,606,613 B2 | 10/2009 | Simon |
| 7,630,753 B2 | 12/2009 | Simon |
| 7,634,122 B2 | 12/2009 | Bertram |
| 7,660,623 B2 | 2/2010 | Hunter |
| 7,697,972 B2 | 4/2010 | Verard |
| 7,751,865 B2 | 7/2010 | Jascob et al. |
| 7,776,000 B2 | 8/2010 | Schaffrath |
| 7,803,164 B2 | 9/2010 | Gielen |
| 7,831,292 B2 | 11/2010 | Quaid |
| 7,835,778 B2 | 11/2010 | Foley |
| 7,835,784 B2 | 11/2010 | Mire |
| 7,840,253 B2 | 11/2010 | Tremblay |
| 7,879,045 B2 | 2/2011 | Gielen |
| 7,925,328 B2 | 4/2011 | Urquhart |
| 7,957,831 B2 | 6/2011 | Isaacs |
| 3,010,177 A1 | 8/2011 | Csavoy |
| 3,010,180 A1 | 8/2011 | Arthur |
| 8,018,456 B2 | 9/2011 | Blumhofer |
| 8,031,922 B2 | 10/2011 | Haimerl |
| 8,108,025 B2 | 1/2012 | Csavoy |
| 8,112,292 B2 | 2/2012 | Simon |
| 8,150,494 B2 | 4/2012 | Simon |
| 8,175,365 B2 | 5/2012 | Edlauer |
| 8,218,846 B2 | 7/2012 | Trumer |
| 8,233,963 B2 | 7/2012 | Hartmann |
| 8,238,631 B2 | 8/2012 | Hartmann |
| 8,239,001 B2 | 8/2012 | Verard |
| 8,295,909 B2 | 10/2012 | Goldbach |
| 8,311,611 B2 | 11/2012 | Csavoy |
| 8,320,991 B2 | 11/2012 | Jascob |
| 8,340,751 B2 | 12/2012 | Markowitz |
| 8,467,852 B2 | 6/2013 | Csavoy |
| 8,494,613 B2 | 7/2013 | Markowitz |
| 8,494,614 B2 | 7/2013 | Markowitz |
| 8,503,745 B2 | 8/2013 | Simon |
| 8,538,539 B2 | 9/2013 | Gharib et al. |
| 8,548,579 B2 | 10/2013 | Gharib et al. |
| 8,549,888 B2 | 10/2013 | Isaacs |
| 8,550,994 B2 | 10/2013 | Miles et al. |
| 8,556,808 B2 | 10/2013 | Miles et al. |
| 8,562,521 B2 | 10/2013 | Miles et al. |
| 8,591,432 B2 | 11/2013 | Pimenta et al. |
| 8,597,211 B2 | 12/2013 | Berlinger |
| 8,602,982 B2 | 12/2013 | Miles et al. |
| 8,628,469 B2 | 1/2014 | Miles et al. |
| 8,634,904 B2 | 1/2014 | Kaula et al. |
| 8,663,100 B2 | 3/2014 | Miles et al. |
| 8,672,840 B2 | 3/2014 | Miles et al. |
| 8,679,006 B2 | 3/2014 | Miles et al. |
| 8,688,409 B2 | 4/2014 | Tuma |
| 8,696,559 B2 | 4/2014 | Miles et al. |
| 8,708,899 B2 | 4/2014 | Miles et al. |
| 8,725,235 B2 | 5/2014 | Gielen |
| 8,737,708 B2 | 5/2014 | Hartmann |
| 8,738,123 B2 | 5/2014 | Gharib et al. |
| 8,744,819 B2 | 6/2014 | Rodriguez Y Baena et al. |
| 8,747,307 B2 | 6/2014 | Miles et al. |
| 8,753,271 B1 | 6/2014 | Miles et al. |
| 8,764,649 B2 | 7/2014 | Miles et al. |
| 8,768,450 B2 | 7/2014 | Gharib et al. |
| 8,784,330 B1 | 7/2014 | Scholl et al. |
| 8,821,396 B1 | 9/2014 | Miles et al. |
| 8,845,656 B2 | 9/2014 | Skakoon |
| 8,942,801 B2 | 1/2015 | Miles et al. |
| 8,945,004 B2 | 2/2015 | Miles et al. |
| 8,956,283 B2 | 2/2015 | Miles et al. |
| 8,971,495 B2 | 3/2015 | Shah |
| 8,977,352 B2 | 3/2015 | Gharib et al. |
| 8,989,866 B2 | 3/2015 | Gharib et al. |
| 8,992,580 B2 | 3/2015 | Bar |
| 9,037,250 B2 | 5/2015 | Kaula et al. |
| 9,044,269 B2 | 6/2015 | Woerlein |
| 9,095,375 B2 | 8/2015 | Haimerl |
| 9,125,680 B2 | 9/2015 | Kostrzewski |
| 9,138,204 B2 | 9/2015 | Koenig |
| 9,161,799 B2 | 10/2015 | Benson |
| 9,198,707 B2 | 12/2015 | Mckay |
| 9,220,573 B2 | 12/2015 | Kendrick |
| 9,237,931 B2 | 1/2016 | Gowda |
| 9,265,589 B2 | 2/2016 | Hartmann |
| 9,289,270 B2 | 3/2016 | Gielen |
| 9,311,335 B2 | 4/2016 | Simon |
| 9,439,623 B2 | 9/2016 | Frank |
| 9,468,412 B2 | 10/2016 | Hamadeh |
| 9,486,295 B2 | 11/2016 | Stefan |
| 9,498,182 B2 | 11/2016 | Case |
| 9,504,531 B2 | 11/2016 | Teichman |
| 9,508,149 B2 | 11/2016 | Simon |
| 9,642,560 B2 | 5/2017 | Schubert |
| 9,652,591 B2 | 5/2017 | Moctezuma De La Barrera |
| 9,668,820 B2 | 6/2017 | Neubauer |
| 9,675,424 B2 | 6/2017 | Jascob |
| 9,681,925 B2 | 6/2017 | Azar |
| 9,697,600 B2 | 7/2017 | Keuchel |
| 9,717,442 B2 | 8/2017 | Jacobsen |
| 9,717,898 B2 | 8/2017 | Thompson-Nauman |
| 9,724,165 B2 | 8/2017 | Arata |
| 9,775,681 B2 | 10/2017 | Quaid |
| 9,820,818 B2 | 11/2017 | Malackowski |
| 9,943,369 B2 | 4/2018 | Heigl |
| 9,974,615 B2 | 5/2018 | Woerlein |
| 10,016,243 B2 | 7/2018 | Esterberg |
| 10,055,848 B2 | 8/2018 | Gassner |
| 10,105,168 B2 | 10/2018 | Blau |
| 10,143,839 B1 | 12/2018 | Christie |
| 10,165,981 B2 | 1/2019 | Schoepp |
| 10,179,031 B2 | 1/2019 | Haimerl |
| 10,191,615 B2 | 1/2019 | Helm |
| 10,297,042 B2 | 5/2019 | Berlinger |
| 10,357,315 B2 | 7/2019 | Otto |
| 10,363,102 B2 | 7/2019 | Abovitz |
| 10,388,066 B2 | 8/2019 | Dorian |
| 10,413,752 B2 | 9/2019 | Berlinger |
| 10,456,204 B2 | 10/2019 | Park |
| 10,478,254 B2 | 11/2019 | Krimsky |
| 10,485,617 B2 | 11/2019 | Crawford |
| 10,492,868 B2 | 12/2019 | Hartmann |
| 10,492,875 B2 | 12/2019 | Janik |
| 10,512,522 B2 | 12/2019 | Verard |
| 10,531,814 B2 | 1/2020 | Reddy |
| 10,531,925 B2 | 1/2020 | Malackowski |
| 10,531,926 B2 | 1/2020 | Roessler |
| 10,561,345 B2 | 2/2020 | Brack |
| 10,575,755 B2 | 3/2020 | Breisacher |
| 10,653,497 B2 | 5/2020 | Crawford |
| 10,660,711 B2 | 5/2020 | Moctezuma De La Barrera |
| 10,667,864 B2 | 6/2020 | Feilkas |
| 10,667,868 B2 | 6/2020 | Malackowski |
| 10,675,094 B2 | 6/2020 | Crawford |
| 10,758,315 B2 | 9/2020 | Johnson |
| 10,799,298 B2 | 10/2020 | Crawford |
| 10,813,704 B2 | 10/2020 | Kostrzewski |
| 10,828,113 B2 | 11/2020 | Melkent |
| 2001/0044624 A1 | 11/2001 | Seraj |
| 2004/0147837 A1 | 7/2004 | Macaulay |
| 2004/0220581 A1 | 11/2004 | Foley |
| 2005/0021031 A1 | 1/2005 | Foley |
| 2006/0036189 A1 | 2/2006 | Martinelli |
| 2006/0094958 A1 | 5/2006 | Marquart |
| 2007/0293721 A1 | 12/2007 | Gilboa |
| 2008/0118135 A1 | 5/2008 | Dorian |
| 2008/0200794 A1 | 8/2008 | Teichman |
| 2008/0255442 A1 | 10/2008 | Ashby |
| 2008/0262342 A1 | 10/2008 | Dorian |
| 2008/0287781 A1 | 11/2008 | Revie |

(56) References Cited

U.S. PATENT DOCUMENTS

| | | |
|---|---|---|
| 2009/0264738 A1 | 10/2009 | Markowitz |
| 2009/0264751 A1 | 10/2009 | Markowitz |
| 2009/0297001 A1 | 12/2009 | Markowitz |
| 2010/0030219 A1 | 2/2010 | Lerner |
| 2010/0034449 A1 | 2/2010 | Dorian |
| 2010/0152571 A1 | 6/2010 | Hartmann |
| 2010/0172557 A1 | 7/2010 | Richard |
| 2010/0192961 A1 | 8/2010 | Amiot |
| 2010/0228117 A1 | 9/2010 | Hartmann |
| 2010/0249576 A1 | 9/2010 | Askarinya |
| 2010/0249581 A1 | 9/2010 | McCombs |
| 2011/0004224 A1 | 1/2011 | Daigneault |
| 2011/0004259 A1 | 1/2011 | Stallings |
| 2011/0015521 A1 | 1/2011 | Faul |
| 2011/0237935 A1 | 9/2011 | Kalpin |
| 2011/0257653 A1 | 10/2011 | Hughes et al. |
| 2012/0197108 A1 | 8/2012 | Hartmann |
| 2012/0197110 A1 | 8/2012 | Hartmann |
| 2012/0220859 A1 | 8/2012 | Amiot |
| 2012/0221017 A1 | 8/2012 | Bonutti |
| 2012/0232377 A1 | 9/2012 | Nottmeier |
| 2012/0323247 A1 | 12/2012 | Bettenga |
| 2012/0330135 A1 | 12/2012 | Millahn |
| 2013/0102878 A1 | 4/2013 | Burg |
| 2013/0131504 A1 | 5/2013 | Daon |
| 2013/0131505 A1 | 5/2013 | Daon |
| 2013/0137972 A1 | 5/2013 | Malackowski |
| 2013/0150863 A1 | 6/2013 | Baumgartner |
| 2013/0218216 A1 | 8/2013 | Mast |
| 2013/0317351 A1 | 11/2013 | Case |
| 2013/0317363 A1 | 11/2013 | Case |
| 2013/0331686 A1 | 12/2013 | Freysinger |
| 2014/0024927 A1 | 1/2014 | Piferi |
| 2014/0039517 A1 | 2/2014 | Gene |
| 2014/0051980 A1 | 2/2014 | Frigg |
| 2014/0148692 A1 | 5/2014 | Hartmann |
| 2014/0171962 A1 | 6/2014 | Kang |
| 2015/0025367 A1 | 1/2015 | Malackowski |
| 2015/0031985 A1 | 1/2015 | Reddy |
| 2015/0073269 A1 | 3/2015 | Stopek |
| 2015/0094736 A1 | 4/2015 | Malackowski |
| 2015/0132720 A1 | 5/2015 | Daon |
| 2015/0147714 A1 | 5/2015 | Daon |
| 2015/0150641 A1 | 6/2015 | Daon |
| 2015/0150692 A1 | 6/2015 | Lye |
| 2015/0182293 A1* | 7/2015 | Yang .................. A61B 17/1703 600/424 |
| 2015/0182296 A1 | 7/2015 | Daon |
| 2015/0209119 A1 | 7/2015 | Theodore |
| 2016/0120609 A1 | 5/2016 | Jacobsen |
| 2016/0128789 A1 | 5/2016 | Kostrzewski |
| 2016/0174873 A1 | 6/2016 | Greenburg |
| 2016/0220320 A1 | 8/2016 | Crawford |
| 2016/0278864 A1 | 9/2016 | Paitel |
| 2016/0278875 A1 | 9/2016 | Crawford |
| 2016/0310218 A1 | 10/2016 | Ruckel |
| 2016/0354160 A1 | 12/2016 | Crowley |
| 2016/0371883 A1 | 12/2016 | Merkine |
| 2017/0007334 A1 | 1/2017 | Crawford |
| 2017/0020491 A1 | 1/2017 | Ogawa |
| 2017/0020630 A1 | 1/2017 | Johnson |
| 2017/0112411 A1 | 4/2017 | Costello |
| 2017/0119339 A1 | 5/2017 | Johnson |
| 2017/0172669 A1 | 6/2017 | Berkowitz |
| 2017/0231702 A1 | 8/2017 | Crawford |
| 2017/0239003 A1 | 8/2017 | Crawford |
| 2017/0239007 A1 | 8/2017 | Crawford |
| 2017/0245951 A1 | 8/2017 | Crawford |
| 2017/0311880 A1 | 11/2017 | Jacobsen |
| 2017/0348061 A1 | 12/2017 | Joshi |
| 2018/0153622 A1 | 6/2018 | Dohmen |
| 2018/0200002 A1 | 7/2018 | Kostrzewski |
| 2018/0217734 A1 | 8/2018 | Koenig |
| 2018/0228623 A1 | 8/2018 | Benson |
| 2018/0263714 A1 | 9/2018 | Kostrzewski |
| 2018/0296283 A1 | 10/2018 | Crawford |
| 2018/0325608 A1 | 11/2018 | Kang |
| 2018/0333207 A1 | 11/2018 | Moctezuma De La Barrera |
| 2018/0367765 A1 | 12/2018 | Stefan |
| 2019/0021795 A1 | 1/2019 | Crawford |
| 2019/0021800 A1 | 1/2019 | Crawford |
| 2019/0029765 A1 | 1/2019 | Crawford |
| 2019/0105116 A1 | 4/2019 | Johnson |
| 2019/0239961 A1 | 8/2019 | Birenbaum |
| 2019/0240489 A1 | 8/2019 | Tsay |
| 2019/0269467 A1 | 9/2019 | Forsyth |
| 2019/0274765 A1 | 9/2019 | Crawford |
| 2019/0321108 A1 | 10/2019 | Fadi |
| 2019/0328461 A1 | 10/2019 | Kemp |
| 2019/0357986 A1 | 11/2019 | Morgan |
| 2019/0374289 A1 | 12/2019 | Stawiaski |
| 2020/0030040 A1 | 1/2020 | Kostrzewski |
| 2020/0107877 A1 | 4/2020 | Koblish |
| 2020/0155243 A1 | 5/2020 | Crawford |
| 2020/0170723 A1 | 6/2020 | Crawford |
| 2020/0188032 A1 | 6/2020 | Komp |
| 2020/0188033 A1 | 6/2020 | Komp |
| 2020/0237444 A1 | 7/2020 | Snyder |
| 2020/0237445 A1 | 7/2020 | Snyder |
| 2020/0297251 A1 | 9/2020 | Herrmann |
| 2020/0297426 A1 | 9/2020 | Cameron |
| 2020/0297427 A1 | 9/2020 | Cameron |
| 2020/0297428 A1 | 9/2020 | Hans |
| 2020/0297435 A1 | 9/2020 | Cameron |
| 2020/0305979 A1 | 10/2020 | Crawford |
| 2020/0315737 A1 | 10/2020 | Crawford |
| 2020/0323609 A1 | 10/2020 | Johnson |
| 2020/0323654 A1 | 10/2020 | Marrapode |
| 2020/0330162 A1 | 10/2020 | Gamm |
| 2020/0345424 A1 | 11/2020 | Wolfsberger |
| 2020/0345430 A1 | 11/2020 | Junio |

FOREIGN PATENT DOCUMENTS

| | | |
|---|---|---|
| EP | 1669027 A1 | 6/2006 |
| EP | 1872737 | 1/2008 |
| JP | 2014524776 A | 9/2014 |
| WO | 9915097 | 4/1999 |
| WO | 9929253 | 6/1999 |
| WO | 2008064126 A2 | 5/2008 |
| WO | 2012173890 A2 | 12/2012 |
| WO | 2012177475 A1 | 12/2012 |
| WO | 2016044934 | 3/2016 |

OTHER PUBLICATIONS

Stryker, Integrated Spine Navigation Solution (2016).
Ziehm NaviPort, 3D Interface for Image-Guided Navigation, Ziehm Imaging, 280943 09 / 2016.

* cited by examiner

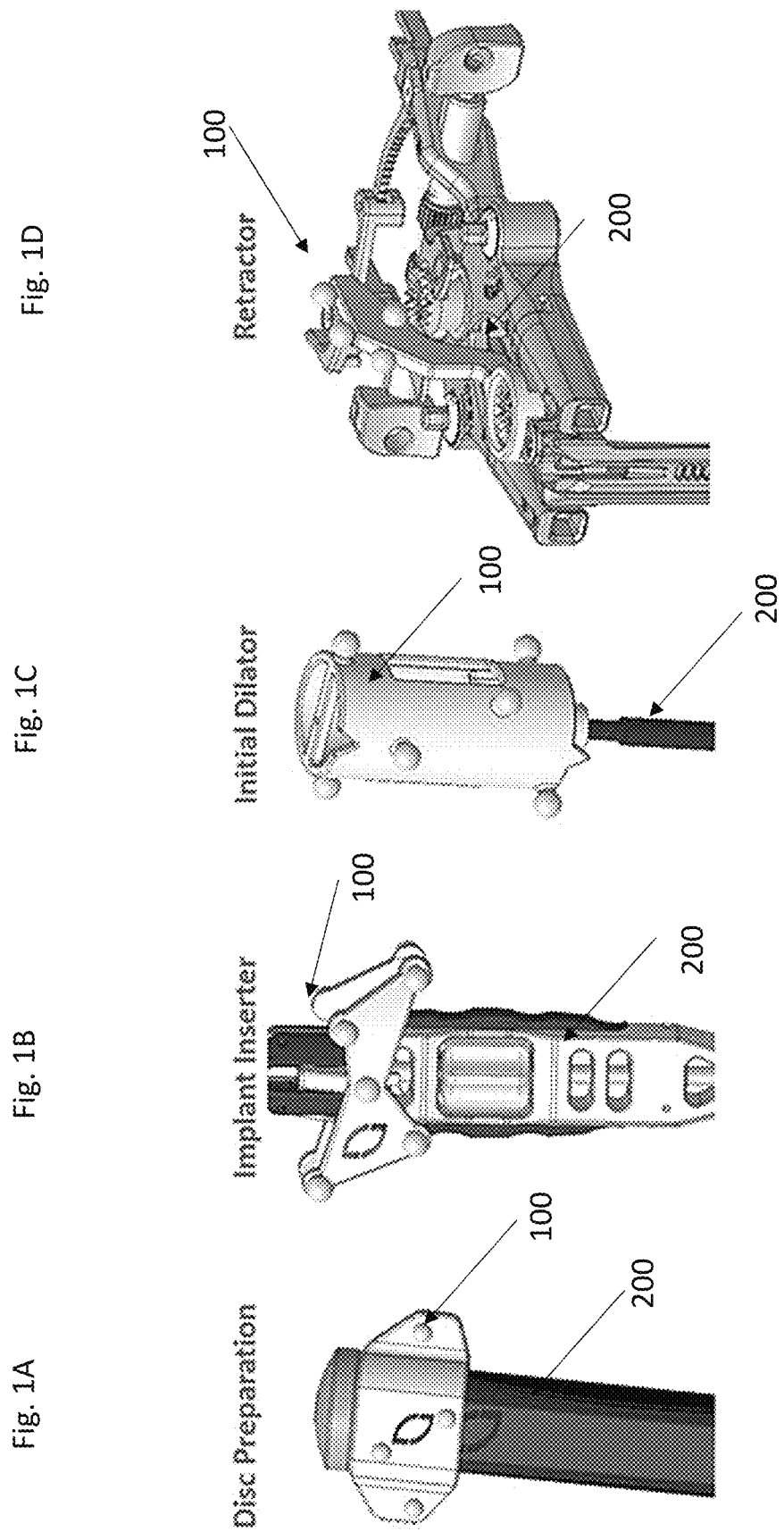

Fig. 4E
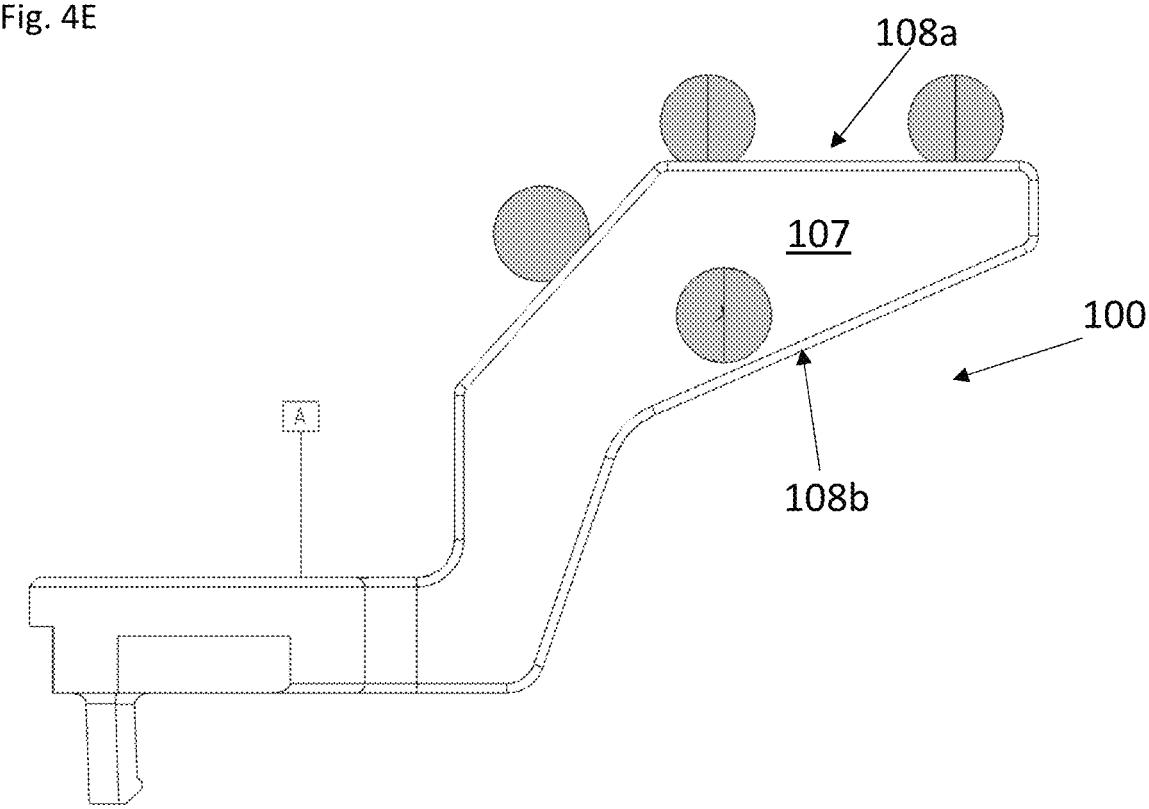
Fig. 4F (right)
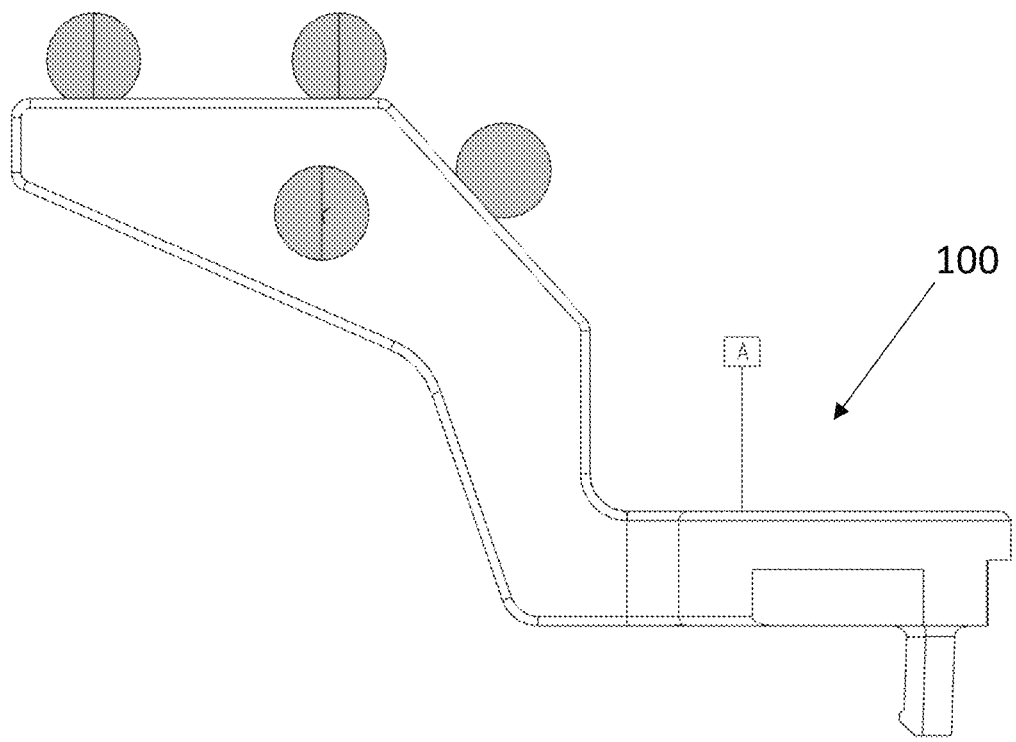

SURGICAL INSTRUMENT TRACKING DEVICES AND RELATED METHODS

CROSS REFERENCE

This application claims priority to U.S. patent application Ser. No. 62/896,128, filed Sep. 5, 2019, the entire contents of which is hereby expressly incorporated by reference into this disclosure as if set forth in its entirety herein.

BACKGROUND

Medical procedures such as minimally invasive surgery (MIS) involve small surgical incisions which reduce surgeon's visualization of patient anatomy and three dimensional (3D) spatial awareness in comparison to traditional "open" techniques. Reduced visualization can lead to reduced location awareness and inaccurate implant placement. Technical challenges of MIS can lead to longer operating room time and/or increased risk of misplaced implants.

SUMMARY

To address technical challenges associated with MIS, surgical navigation systems are implemented in computer assisted surgery or image guided surgery to allow the surgeon to track surgical instruments and use tracking information to directly or indirectly guide the surgical procedure. Surgical navigation systems can use a camera to capture and relay information about the patient's anatomy, and/or position and orientation of the instruments in relation to the patient, for presentation at a digital display, therefore providing fast and accurate feedback to the surgeon's movement during an operation.

The benefits of image-guided surgery using surgical navigation systems may include greater control of the surgical procedure, near real-time feedback on the effect of the intervention, reduced tissue trauma and disruption in gaining access to the anatomical structure. Such image-guided surgery may also allow for: reduced post-operative neural deficits and adverse events. Thus, image-guided surgery using surgical navigation systems can help surgeons perform safer and less invasive procedures and may become a recognized standard of care in managing disorders including cranial, spine, orthopedic, and cardiovascular.

To ensure accurate and reliable functioning of the surgical navigation systems, there is an urgent need for apparatuses and methods that tracks the surgical instruments continuously and accurately with minimal interference to the surgical procedure.

Disclosed herein are apparatuses, systems, and methods for tracking the medical instruments, or more generally, other objects in the operating room, in near real-time during a medical procedure. The apparatuses, systems, and methods herein can include tracking arrays with a plurality of tracking markers. The tracking markers can each be uniquely identified by one or more image capturing devices, e.g., a dual camera system, and the identification of the tracking markers, e.g., at least 3 markers at any time point during an operation, can advantageously allow accurate tracking of the instruments even if the instruments are positioned in an arbitrary location and/or orientation in three-dimension in relation to the image capturing device. The apparatuses, systems, and methods herein also advantageously includes tracking arrays of a shape and size that present less interference to the surgeon's movement when attached to a medical instrument than traditional tracking arrays. Additionally, the tracking arrays herein include attachment features that releasably attach the tracking array(s) at a pre-selected location specific to the medical instrument. The location, shape, and/or size of the attachment features of the tracking arrays, together with those of the complementary attachment features on the medical instruments are predetermined so as to advantageously prevent obstruction of the tracking markers by the surgeon and/or the patient during an operation.

In one aspect, disclosed herein is a tracking array for surgical navigation, the tracking array comprising: a three-dimensional structure having an outer surface; a plurality of tracking markers arranged on the outer surface of the tracking array, the plurality of tracking markers is configured to be detectable by an image capturing device; and an attachment feature configured to releasably and securely attach the tracking array to an object. In some cases, the outer surface is three-dimensional. In some cases, the image capturing device comprises one or more optical cameras. In some cases, the image capturing device is an infrared light camera. In some cases, one or more of the plurality of tracking markers comprise a spherical surface. In some cases, one or more of the plurality of tracking markers are configured to reflect an optical signal which is captured by the image capturing device. In some cases, two or more of the plurality of tracking markers comprise an identical shape, size, or both. In some cases, all of the plurality of tracking markers comprises an identical shape, size or both. In some cases, the plurality of tracking markers is positioned on the outer surface so that at least 3, 4, 5, 6, 7, 8, 9, or 10 of the plurality of tracking markers are visible to the image capturing device when the tracking array is rotated with an arbitrary rotation angle in three-dimension. In some cases, the plurality of tracking markers is positioned so that all of the plurality of tracking markers is non-overlapping and visible to the image capturing device when viewed along a proximal-to-distal direction. In some cases, the three-dimensional structure comprises an elongate body, a cavity located therewithin, and a first and a second side wing attached to the elongate body. In some cases, the cavity is configured to allow insertion of the object therethrough, and wherein the attachment feature is located within the cavity. In some cases, the first and second side wings are not symmetrically positioned about a longitudinal axis along a proximal to distal direction. In some cases, the outer surface includes a first flat surface and a second flat surface opposite to each other on the elongate body. In some cases, each of the first and second side wings includes a first and second flat surface opposite to each other. In some cases, the tracking array further includes a concave surface connecting the first flat surface on the elongate body to the first flat surface of the first side wing. In some cases, at least two tracking markers are positioned on each of the first and second flat surface on the elongate body and at least two tracking markers are positioned on each of the first and second side wings, and wherein no tracking marker is positioned on the concave surface. In some cases, the three-dimensional structure comprises a cylindrical body with two windows opposite to each other, a cavity located therewithin the cylindrical body, and a neck region extending along a longitudinal axis beyond a distal edge of the cylindrical body. In some cases, the attachment feature is located within the neck region of the tracking array. In some cases, the cylindrical body comprises a leg extending distally from a distal end of the cylindrical body, and a dent at a proximal end of the cylindrical body for assisting neuro-monitoring. In some cases, the three-dimensional structure comprises a body and a tail portion. In some cases, the attachment feature is positioned at a distal end of the body. In some cases, the plurality of tracking markers is position only at the tail portion. In some cases, the tail portion includes a proximal surface, a first and a second flat side surface opposite to each other, and a distal surface. In some cases, no tracking marker is positioned on the distal surface, and wherein a first tracking marker is placed on the first side wall, and a second tracking marker is placed on the second side wall. In some cases, the first and second tracking markers are at different locations along a proximal-to-distal direction. In some cases, the tracking array includes a first and a second concave wall opposite to each other, and a bridge therebetween. In some cases, the attachment feature is positioned at a distal end of the bridge. In some cases, a proximal end of the first or second concave wall extends more distally than a proximal end of the bridge. In some cases, the bridge comprises no tracking marker thereon.

In another aspect, disclosed herein is a system for surgical navigation, the system comprising: a tracking array comprising: a plurality of tracking markers arranged on an outer surface of the tracking array; and an attachment feature configured to releasably and securely attach the tracking array to an object; and an image capturing device for tracking at least three of the plurality of tracking markers simultaneously; a navigation system that communicates with the image capturing device and generates surgical navigation information based on the tracking of the plurality of tracking markers.

In yet another aspect, disclosed herein is a method for surgical navigation, the method comprising: releasably attaching a tracking array to a medical instrument by engaging the attachment feature of the tracking array with the complementary attachment feature of the medical instrument; tracking the tracking array, by an image capturing device, during a medical procedure thereby generating tracking information; communicating, by the image capturing device, the tracking information to a navigation system; and displaying one or more images of the medical instrument, the tracking array, or both, by a digital display, to a medical professional.

In yet another aspect, disclosed herein is a method for surgical navigation, the method comprising: providing a tracking array with an attachment feature; providing a complementary attachment feature on a medical instrument; allowing a user to releasably attach the tracking array to the medical instrument by engaging the attachment feature of the tracking array with the complementary attachment feature of the medical instrument; and allowing a user to track the tracking array, by an image capturing device, during a medical procedure thereby generating tracking information that is configured to be used to enable tracking of the medical instrument.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows an exemplary embodiment of an array attached to a medical instrument for navigation of the instrument; in this case, an intervertebral disc preparation instrument, in accordance with embodiments herein;

FIG. 1B shows an exemplary embodiment of an array attached to a medical instrument for navigation of the instrument; in this case, an implant inserter, in accordance with embodiments herein;

FIG. 1C shows an exemplary embodiment of an array attached to a medical instrument for navigation of the instrument; in this case, an initial dilator, in accordance with embodiments herein;

FIG. 1D shows an exemplary embodiment of an array attached to a medical instrument for navigation of the instrument; in this case, a retractor, in accordance with embodiments herein;

FIGS. 4C-4H show the front view (FIG. 4C), back view (FIG. 4D), left side view (FIG. 4E), right side view (FIG. 4F), top view (FIG. 2G), and bottom view (FIG. 2H) of the tracking array in FIG. 1D, respectively;

DETAILED DESCRIPTION

Figure 2A:
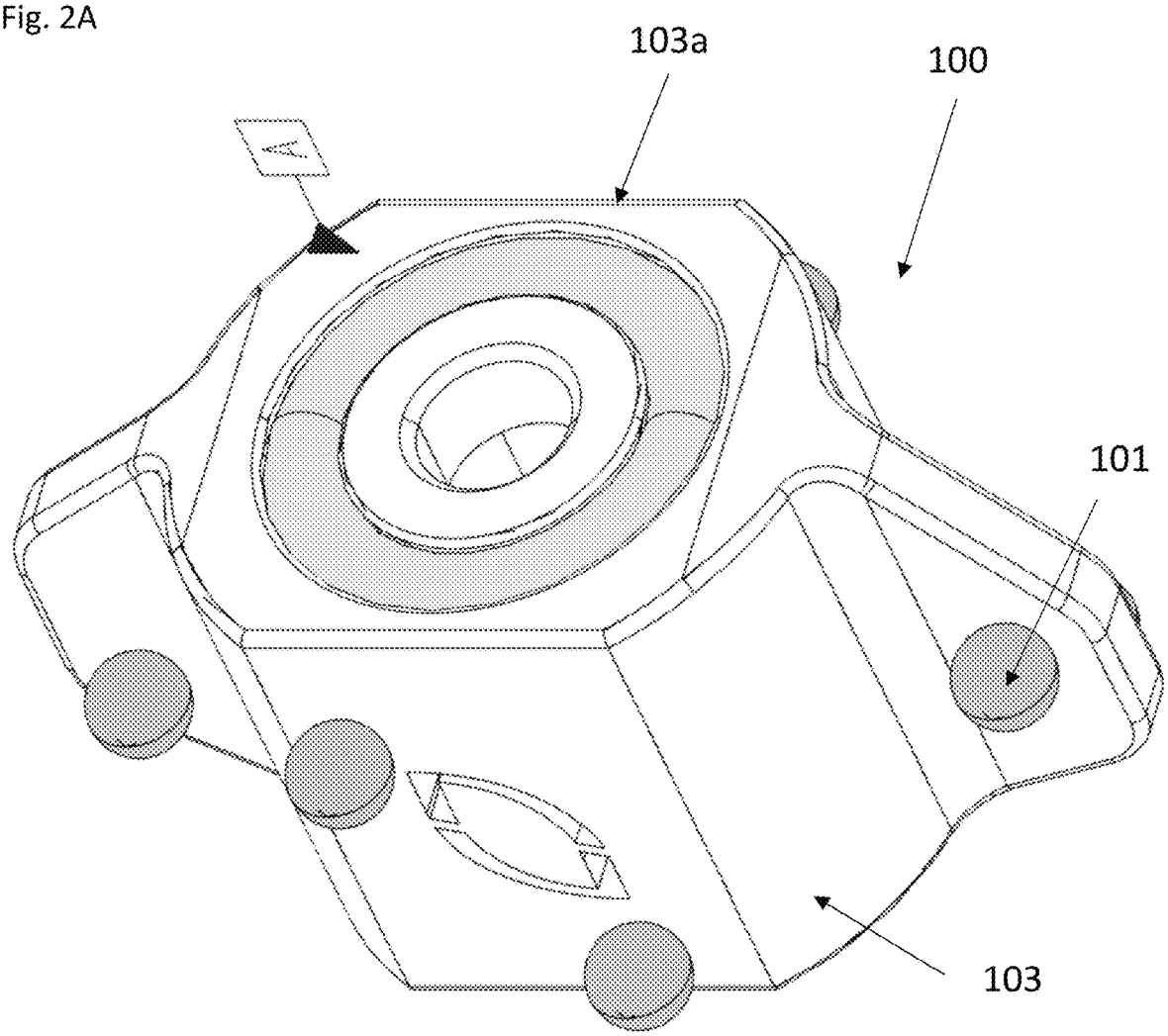
FIGS. 2A-2B show the perspective views of the tracking array in FIG. 1A.
Figure 2B:
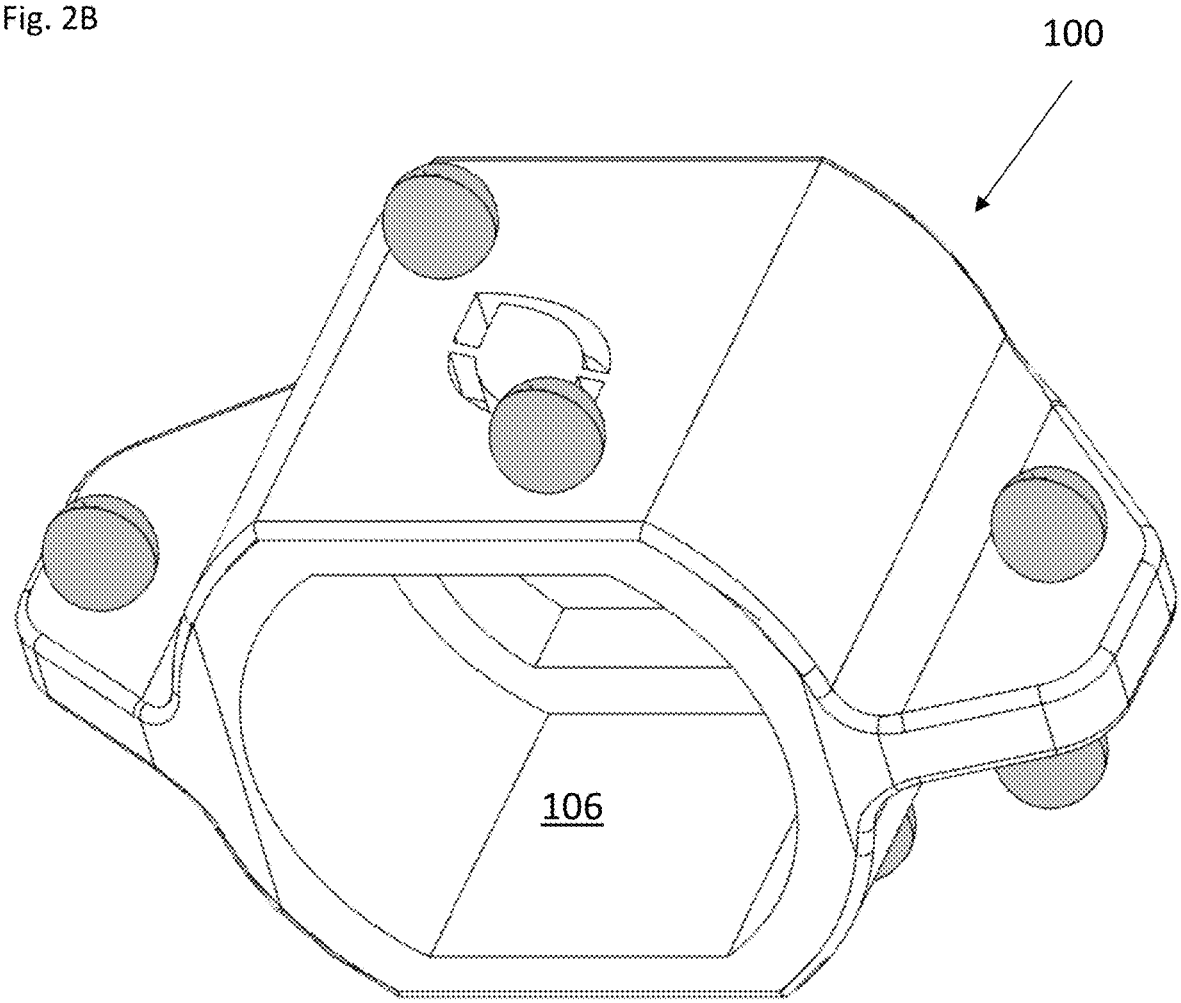

Disclosed herein, in some embodiments, is a tracking array for surgical navigation, the tracking array comprising: a three-dimensional structure having an outer surface; a plurality of tracking markers arranged on the outer surface of the tracking array, the plurality of tracking markers is configured to be detectable by an image capturing device; and an attachment feature configured to releasably and securely attach the tracking array to an object. In some cases, the outer surface is three-dimensional. In some cases, the image capturing device comprises one or more optical cameras. In some cases, the image capturing device is an infrared light camera. In some cases, one or more of the plurality of tracking markers comprise a spherical surface. In some cases, one or more of the plurality of tracking markers are configured to reflect an optical signal which is captured by the image capturing device. In some cases, two or more of the plurality of tracking markers comprise an identical shape, size, or both. In some cases, all of the plurality of tracking markers comprises an identical shape, size or both. In some cases, the plurality of tracking markers is positioned on the outer surface so that at least 3, 4, 5, 6, 7, 8, 9, or 10 of the plurality of tracking markers are visible to the image capturing device when the tracking array is rotated with an arbitrary rotation angle in three-dimension. In some cases, the plurality of tracking markers is positioned so that all of the plurality of tracking markers is non-overlapping and visible to the image capturing device when viewed along a proximal-to-distal direction. In some cases, the three-dimensional structure comprises an elongate body, a cavity located therewithin, and a first and a second side wing attached to the elongate body. In some cases, the cavity is configured to allow insertion of the object therethrough, and wherein the attachment feature is located within the cavity. In some cases, the first and second side wings are not symmetrically positioned about a longitudinal axis along a proximal to distal direction. In some cases, the outer surface includes a first flat surface and a second flat surface opposite to each other on the elongate body. In some cases, each of the first and second side wings includes a first and second flat surface opposite to each other. In some cases, the tracking array further includes a concave surface connecting the first flat surface on the elongate body to the first flat surface of the first side wing. In some cases, at least two tracking markers are positioned on each of the first and second flat surface on the elongate body and at least two tracking marker are positioned on each of the first and second side wings, and wherein no tracking marker is positioned on the concave surface. In some cases, the three-dimensional structure comprises a cylindrical body with two windows opposite to each other, a cavity located therewithin the cylindrical body, and a neck region extending along a longitudinal axis beyond a distal edge of the cylindrical body. In some cases, the attachment feature is located within the neck region of the tracking array. In some cases, the cylindrical body comprises a leg extending distally from a distal end of the cylindrical body, and a dent at a proximal end of the cylindrical body for assisting neuro-monitoring. In some cases, the three-dimensional structure comprises a body and a tail portion. In some cases, the attachment feature is positioned at a distal end of the body. In some cases, the plurality of tracking markers is position only at the tail portion. In some cases, the tail portion includes a proximal surface, a first and a second flat side surface opposite to each other, and a distal surface. In some cases, no tracking marker is positioned on the distal surface, and wherein a first tracking marker is placed on the first side wall, and a second tracking marker is placed on the second side wall. In some cases, the first and second tracking markers are at different location along a proximal-to-distal direction. In some cases, the tracking array includes a first and a second concave wall opposite to each other, and a bridge therebetween. In some cases, the attachment feature is positioned at a distal end of the bridge. In some cases, a proximal end of the first or second concave wall extends more distally than a proximal end of the bridge. In some cases, the bridge comprises no tracking marker thereon.

In some embodiments, disclosed herein is a system for surgical navigation, the system comprising: a tracking array comprising: a plurality of tracking markers arranged on an outer surface of the tracking array; and an attachment feature configured to releasably and securely attach the tracking array to an object; and an image capturing device for tracking at least three of the plurality of tracking markers simultaneously; a navigation system that communicates with the image capturing device and generates surgical navigation information based on the tracking of the plurality of tracking markers.

In some embodiments, disclosed herein is a method for surgical navigation, the method comprising: releasably attaching a tracking array to a medical instrument by engaging the attachment feature of the tracking array with the complementary attachment feature of the medical instrument; tracking the tracking array, by an image capturing device, during a medical procedure thereby generating tracking information; communicating, by the image capturing device, the tracking information to a navigation system; and displaying one or more images of the medical instrument, the tracking array, or both, by a digital display, to a medical professional.

In some embodiments, disclosed herein is a method for surgical navigation, the method comprising: providing a tracking array with an attachment feature; providing a complementary attachment feature on a medical instrument; allowing a user to releasably attach the tracking array to the medical instrument by engaging the attachment feature of the tracking array with the complementary attachment feature of the medical instrument; and allowing a user to track the tracking array, by an image capturing device, during a medical procedure thereby generating tracking information that is configured to be used to enable tracking of the medical instrument.

Certain Terms

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Tracking Arrays

Disclosed herein are tracking arrays that can be used in image guided or computer assisted surgery. Disclosed herein are tracking arrays that can be used with a surgical navigation system for tracking medical instruments. The tracking arrays can be used to track or navigate instruments especially during a medical procedure or surgery.

The tracking array can be made of biocompatible materials including but not limited to plastic, polymer, metal, and alloy. The tracking array may be manufactured via 3D printing, molding or any other method of selection.

In some embodiments, the tracking array 100 disclosed herein includes a 3D structure. The 3D structure includes a frame or an array body 103. The frame or array body may comprise an outer surface 103a at least partly enclosing a cavity 106 therewithin. The frame or array body may be of any 3D size and shape. The size and shape of the frame or array body in any spatial dimension(s) can be customized to accommodate the size and shape of the medical instruments to be attached thereto. In some embodiments, the size and shape may be determined to reduce the increase to the overall size of the instrument and the array yet still enabling coupling of the tracking array to the medical instrument.

Figure 2C:
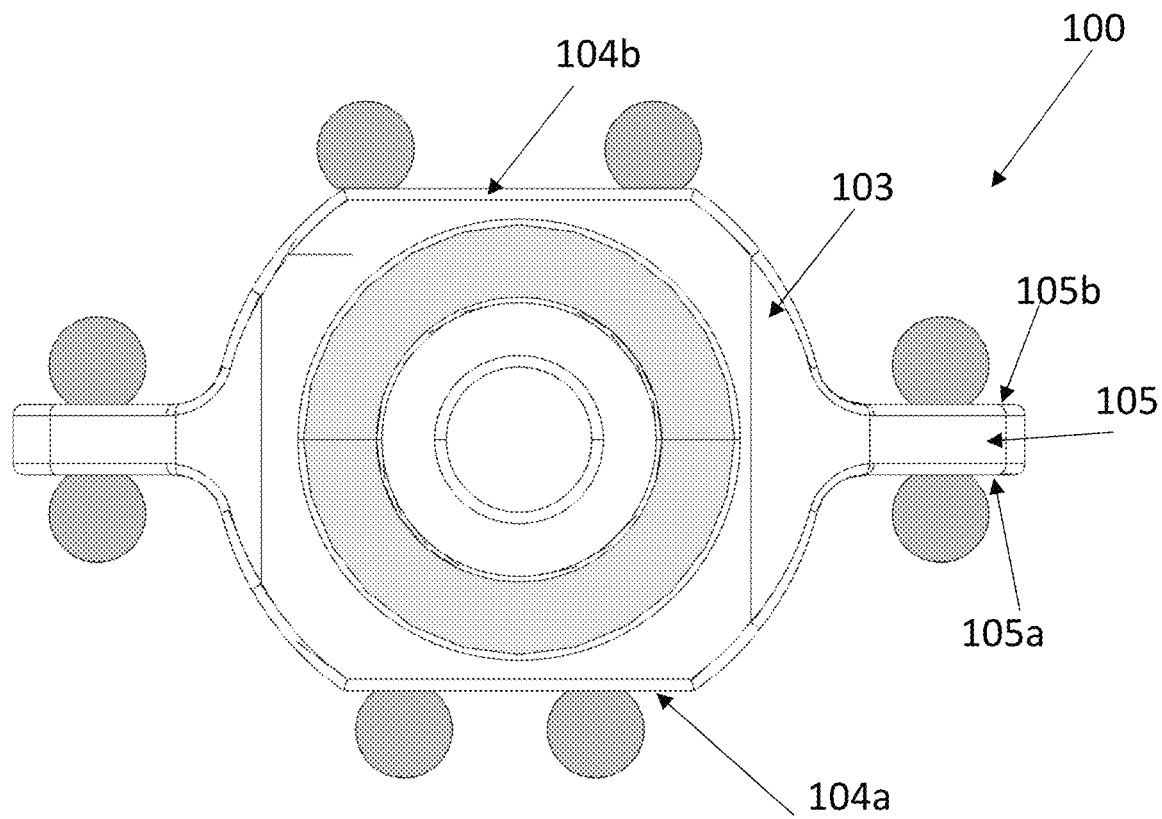
FIGS. 2C-2H show the front view (FIG. 2C), back view (FIG. 2D), left side view (FIG. 2E), right side view (FIG. 2F), top view (FIG. 2G), and bottom view (FIG. 2H) of the tracking array in FIG. 1A, respectively.
Figure 3A:
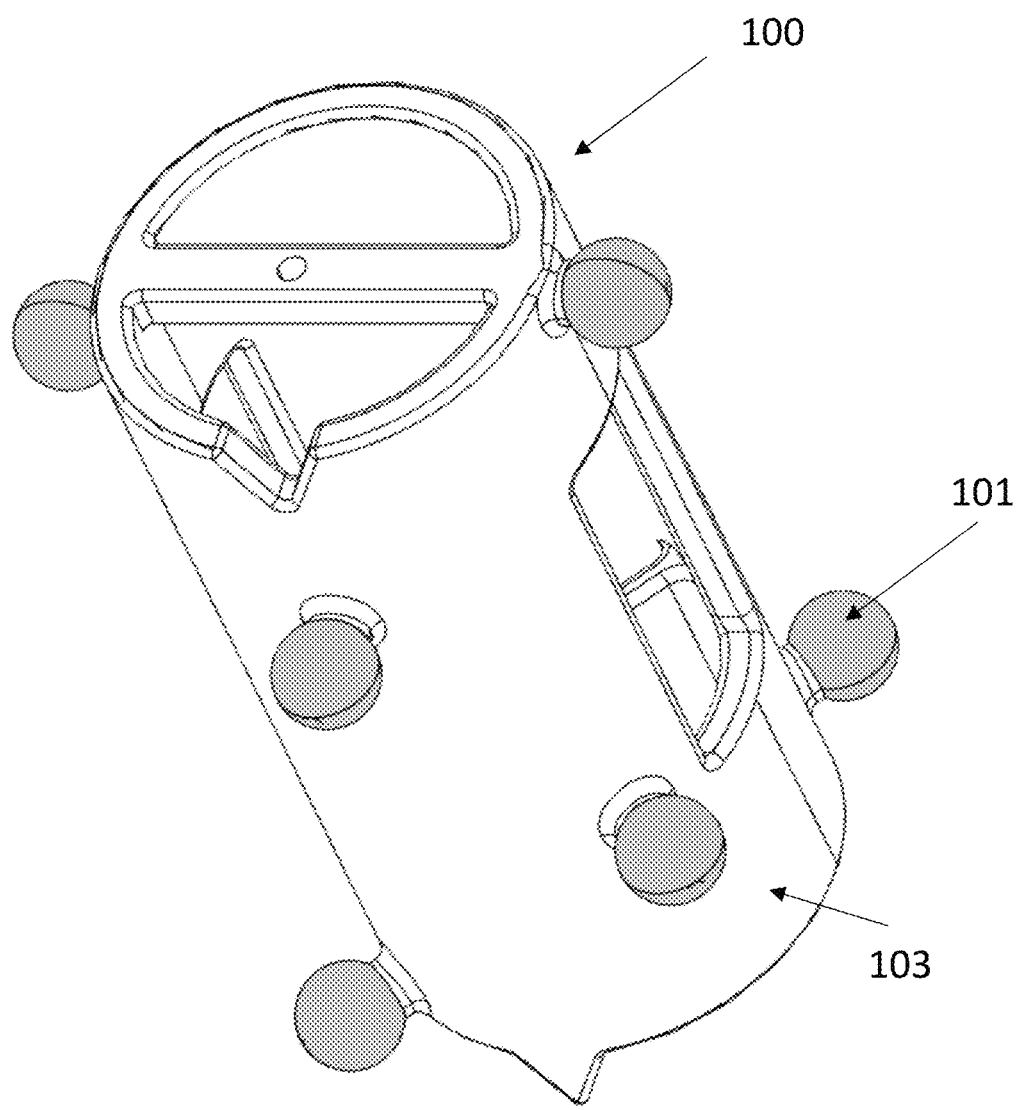
FIGS. 3A-3B show the perspective views of the tracking array in FIG. 1C.
Figure 3B:
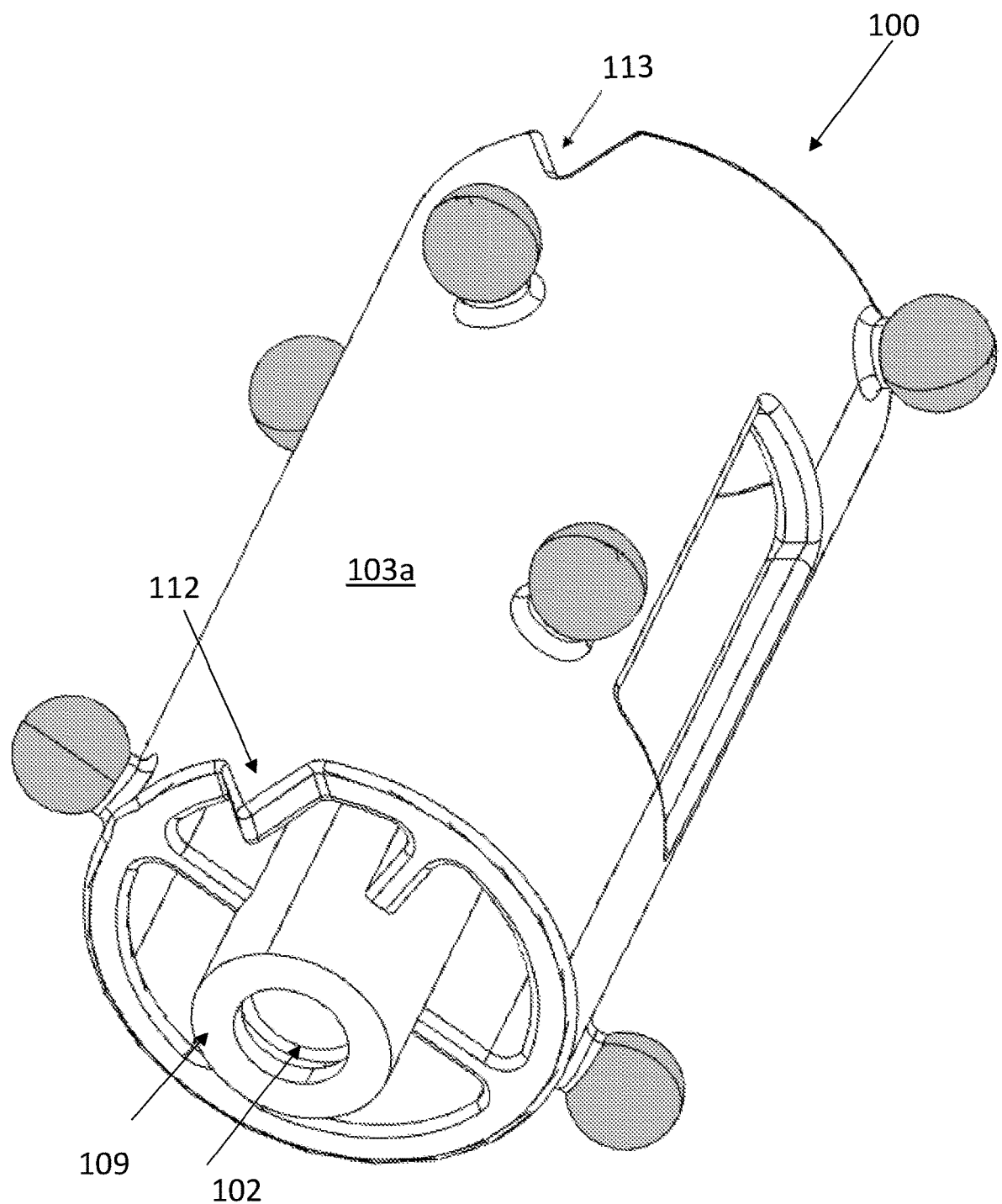
Figure 3C:
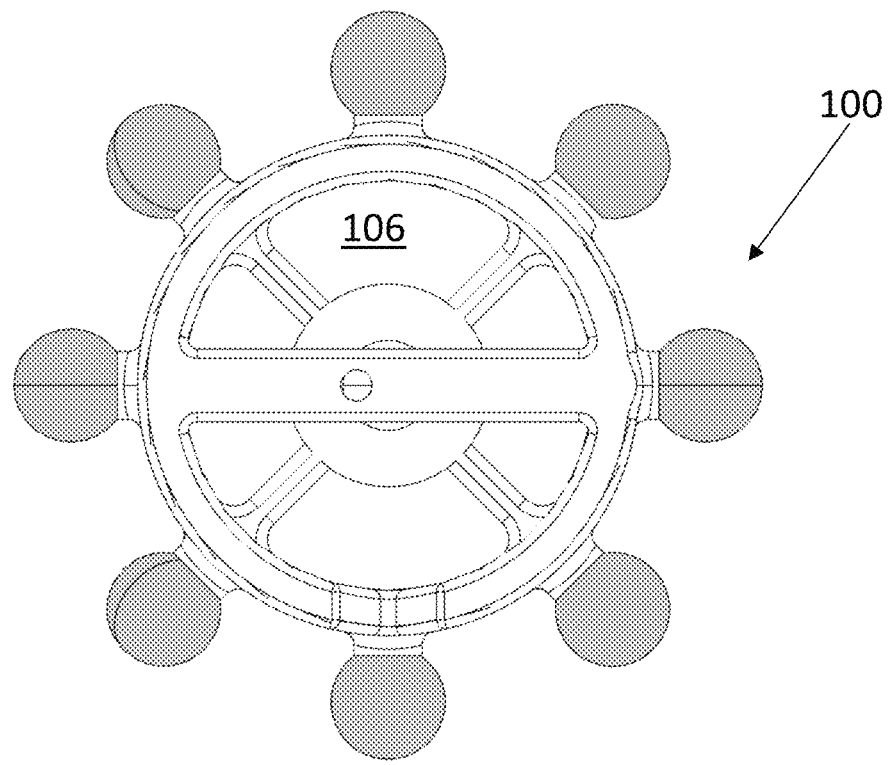
FIGS. 3C-3H show the front view (FIG. 3C), back view (FIG. 3D), left side view (FIG. 3E), right side view (FIG. 3F), top view (FIG. 3G), and bottom view (FIG. 3H) of the tracking array in FIG. 1C, respectively.
Figure 3D:
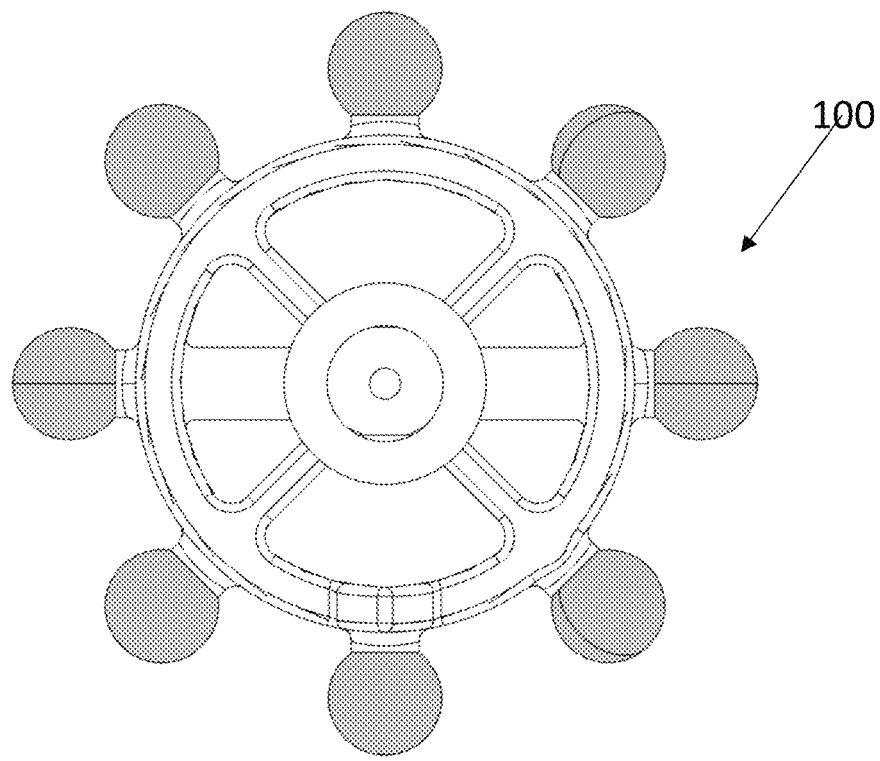
Figure 3E:
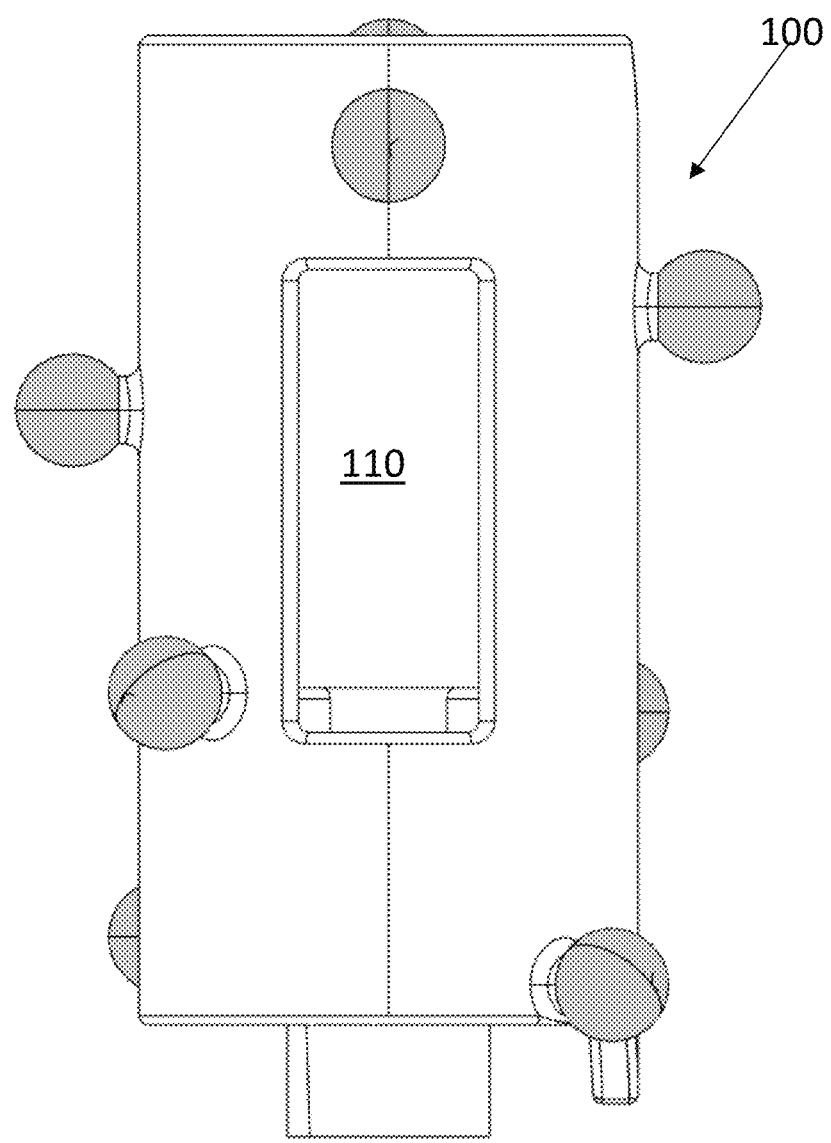
Figure 3F:
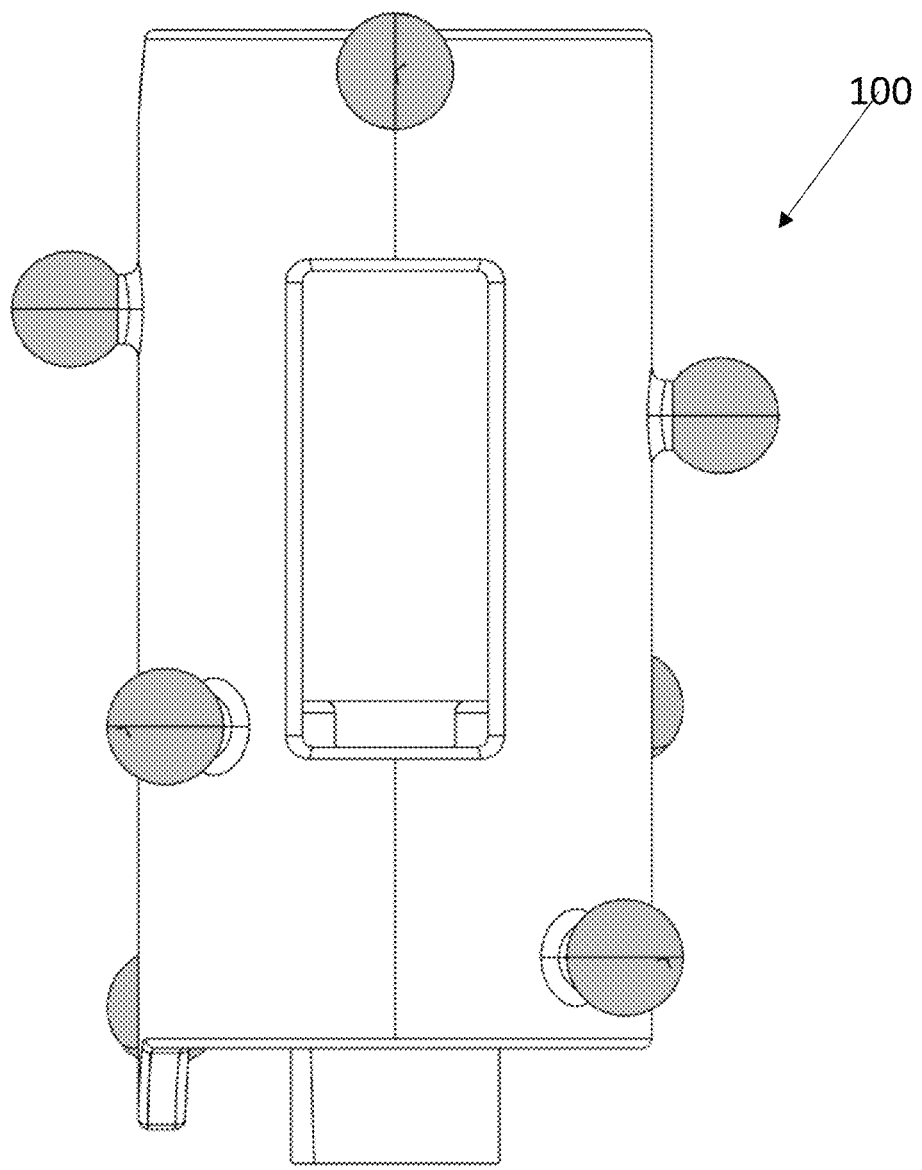
Figure 3G:
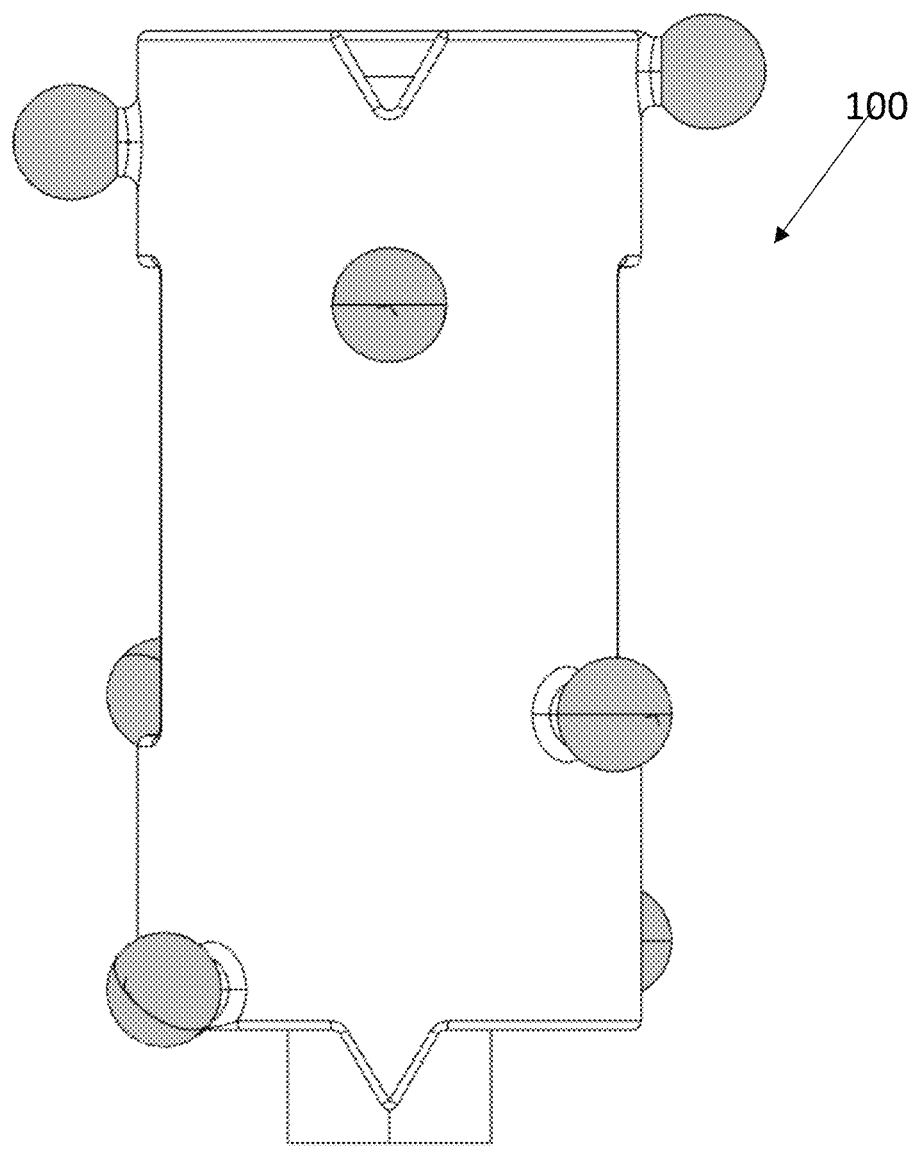
Figure 3H:
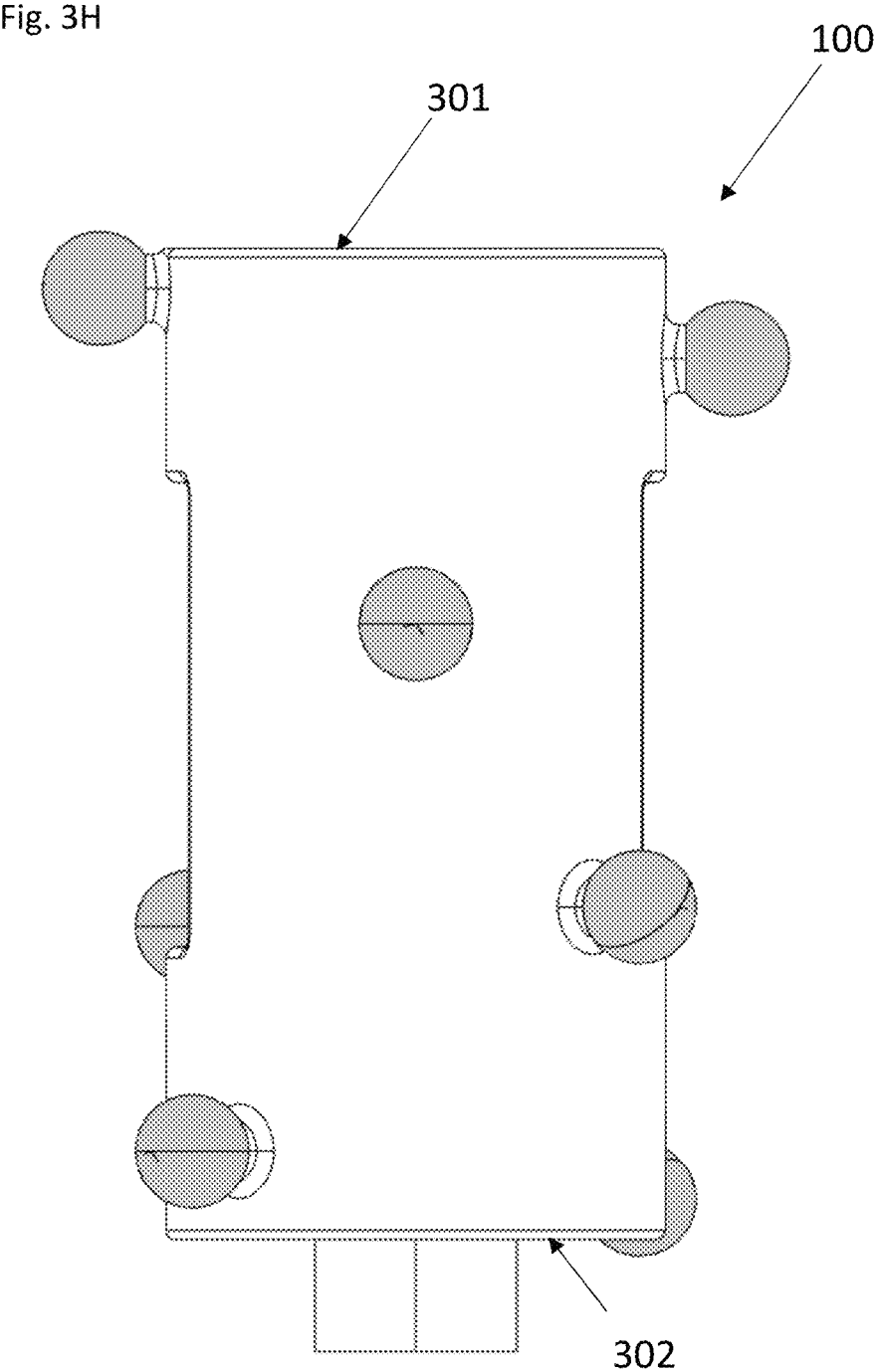
Figure 4A:
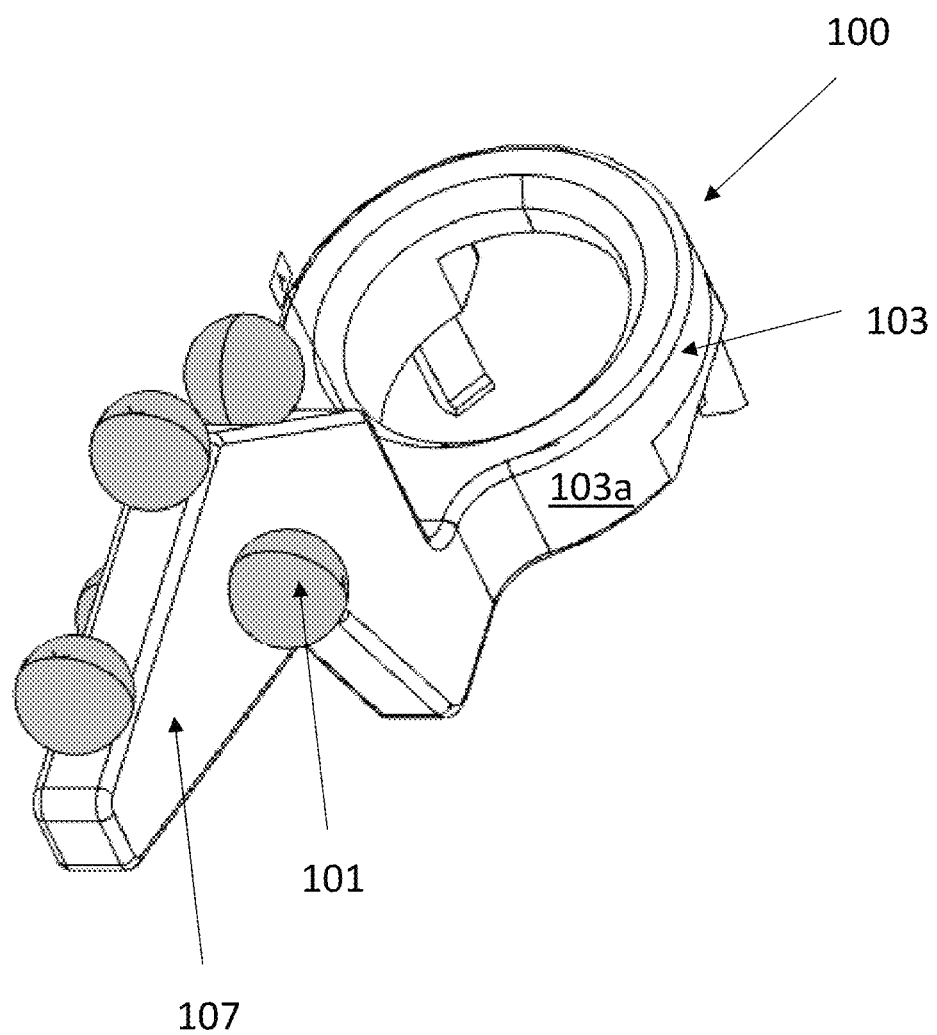
FIGS. 4A-4B show the perspective views of the tracking array in FIG. 1D.
Figure 4B:
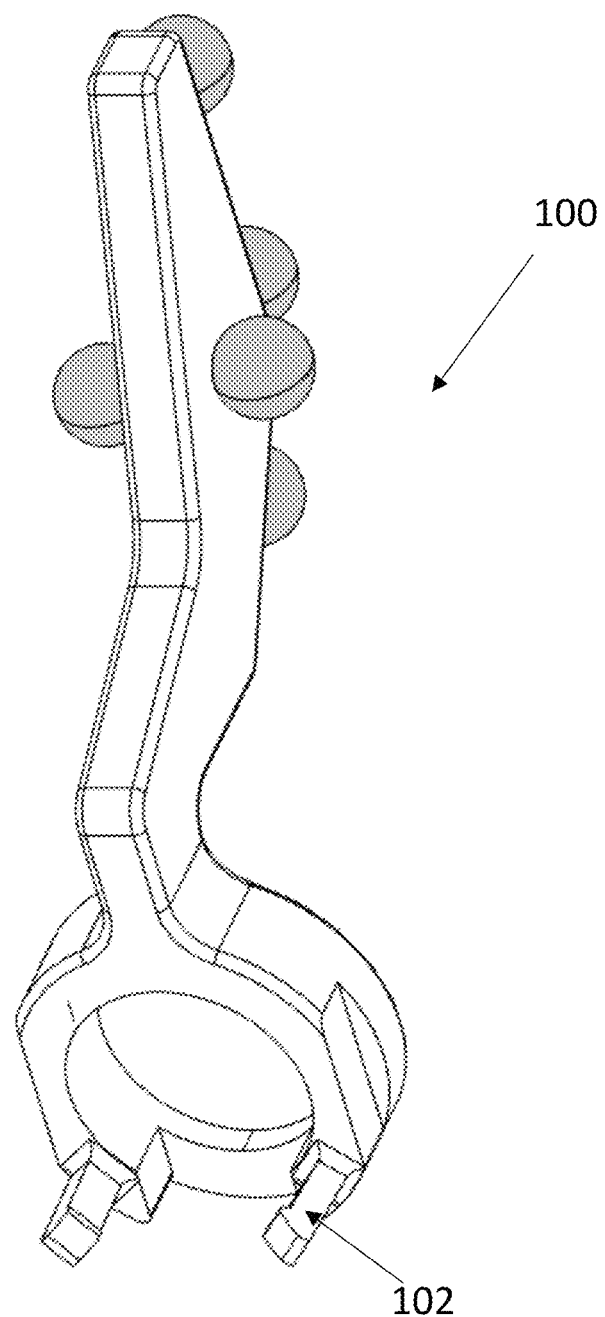
Figure 4C:
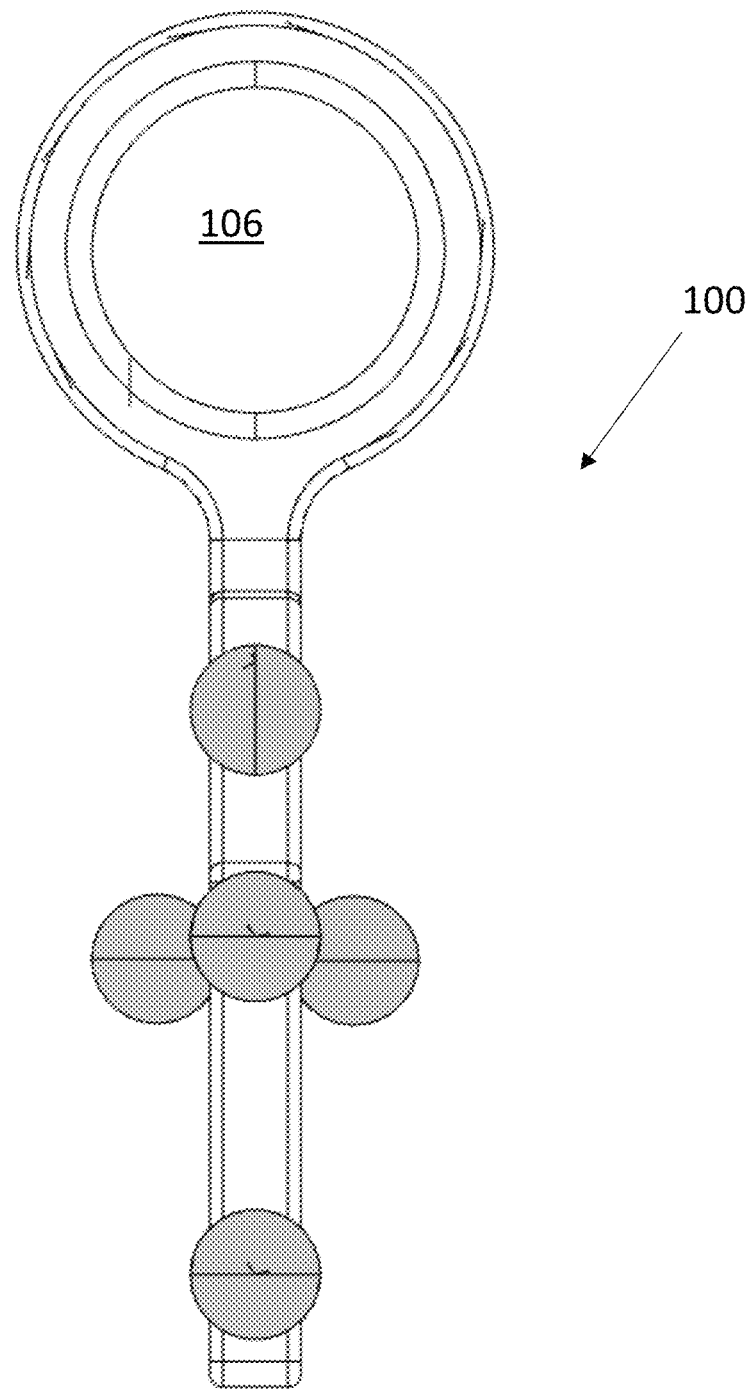
Figure 4D:
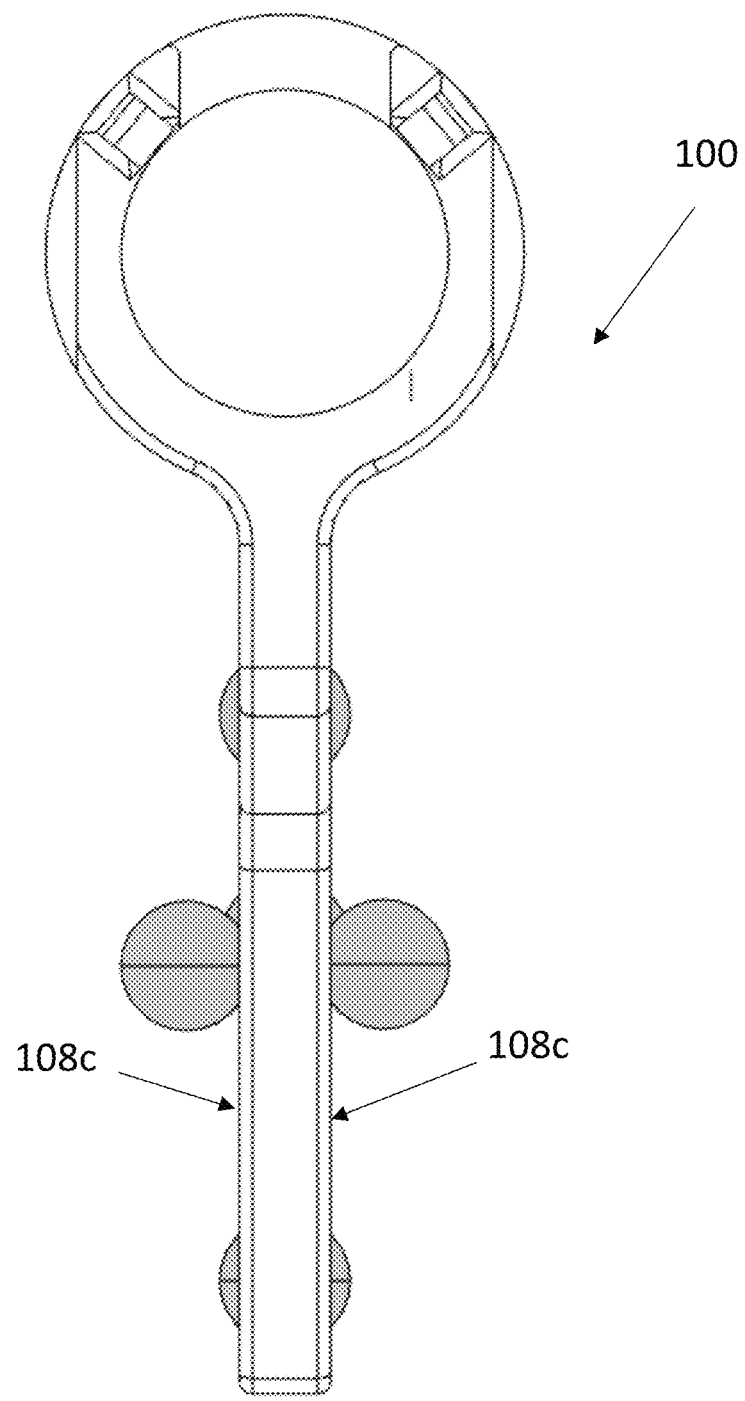
Figure 5A:
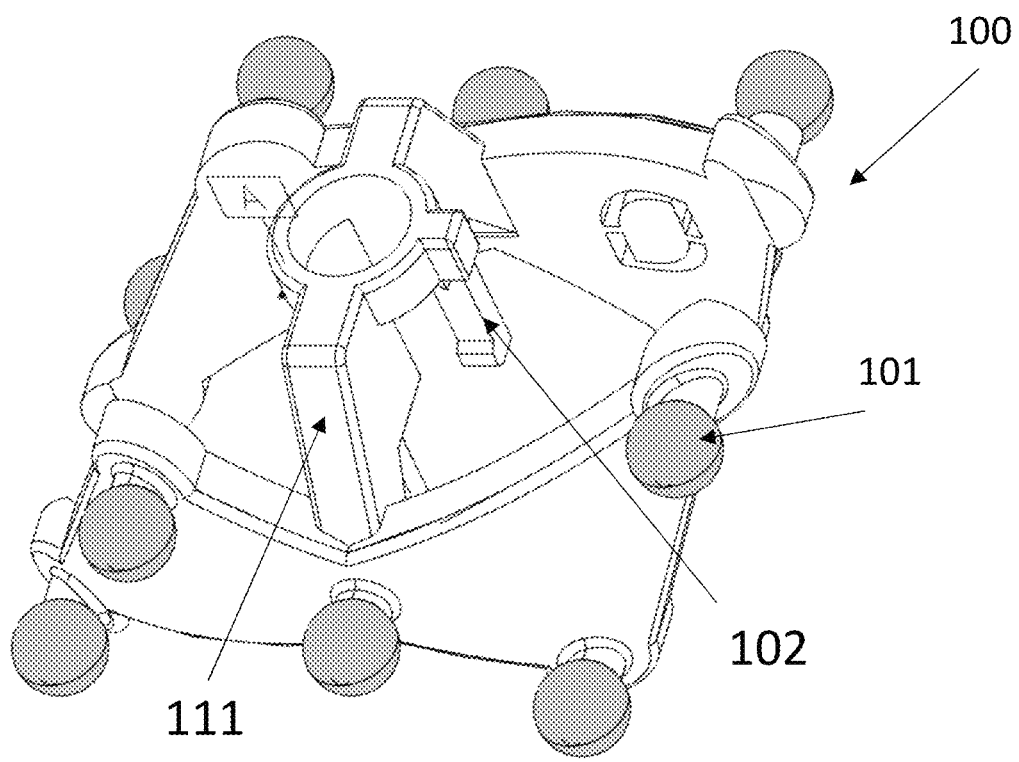
FIGS. 5A-5B show the perspective views of the tracking array in FIG. 1B.
Figure 5B:
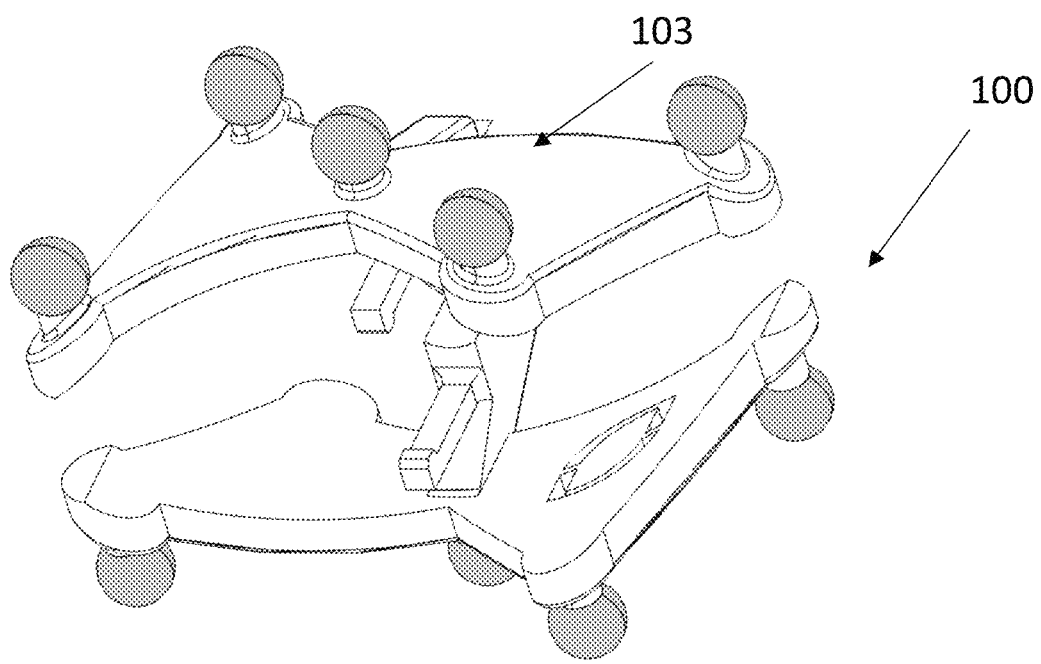
Figure 5C:
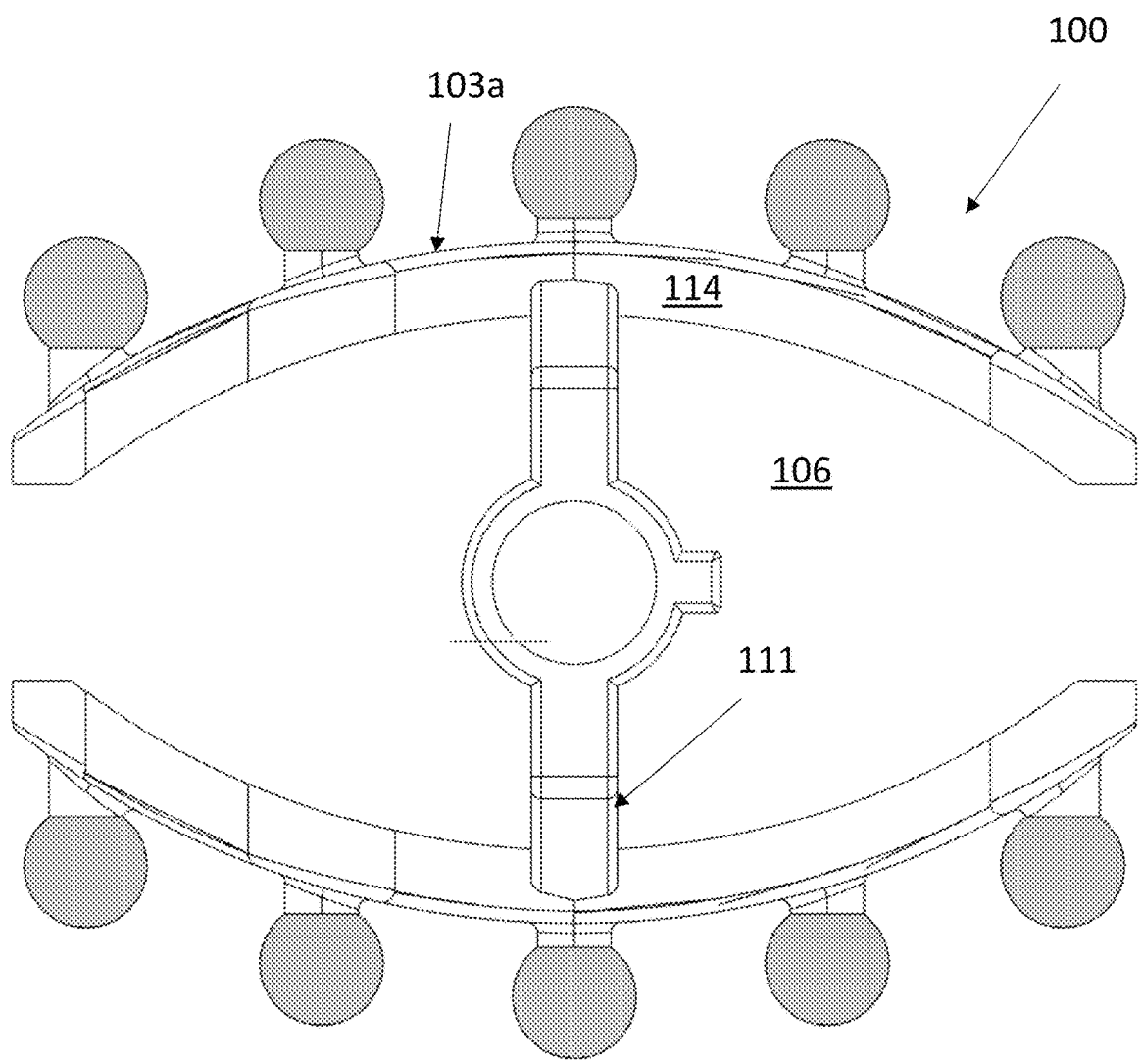
FIGS. 5C-5G show the front view (FIG. 5C), back view (FIG. 5D), left side view (FIG. 5E), right side view (FIG. 5F), top view (FIG. 5G), and bottom view (FIG. 5H) of the tracking array in FIG. 1B, respectively.
Figure 5D:
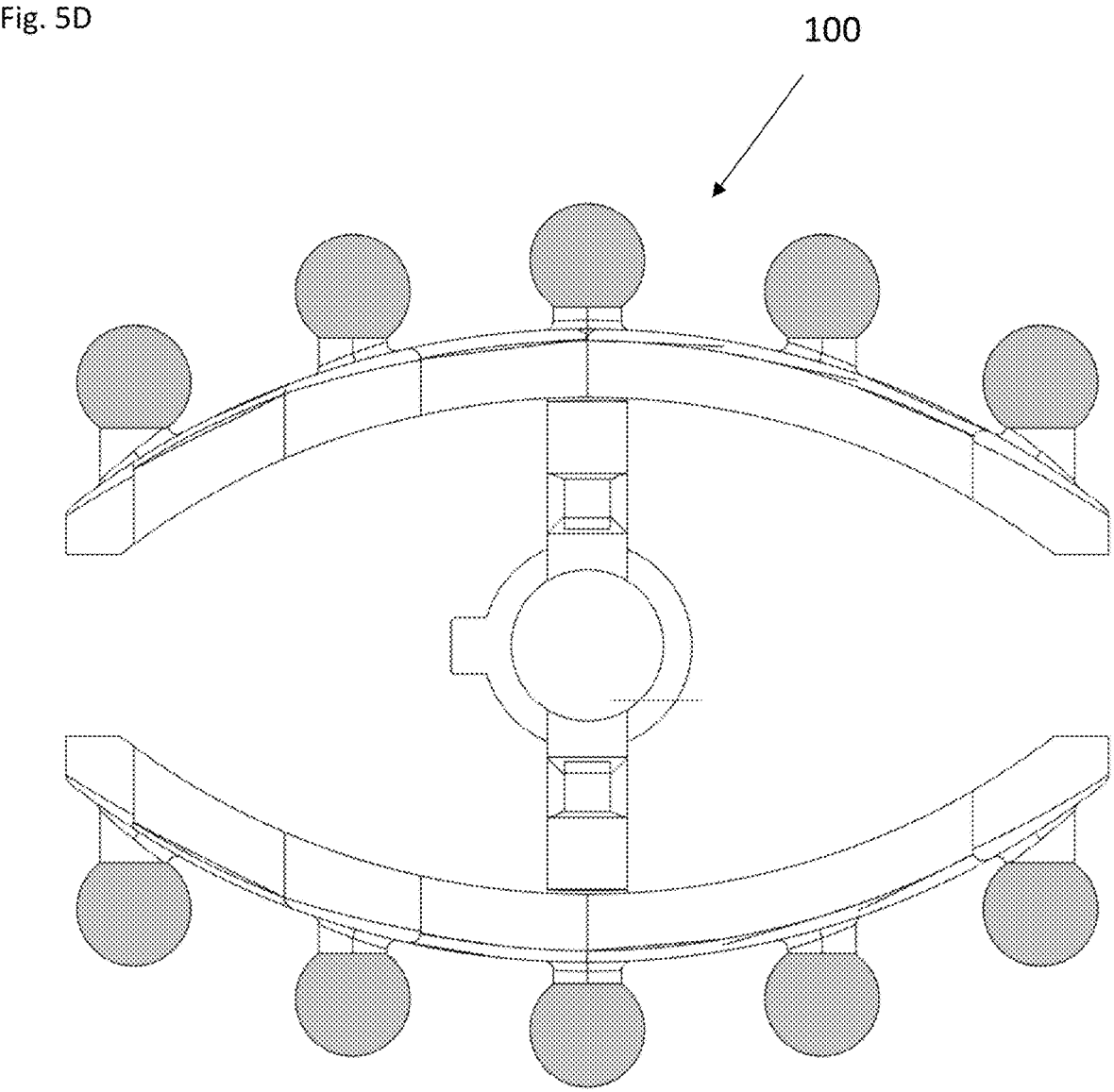
Figure 5E:
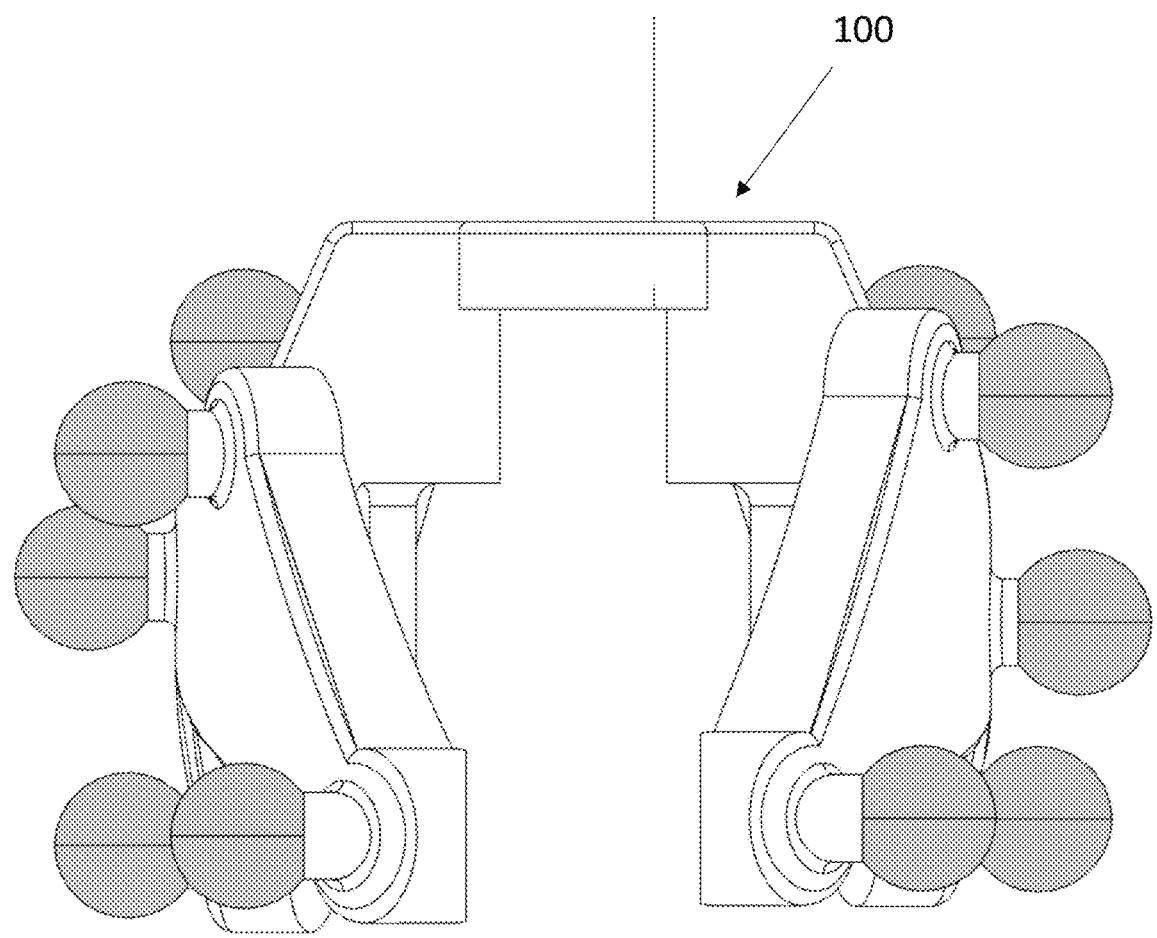
Figure 5F:
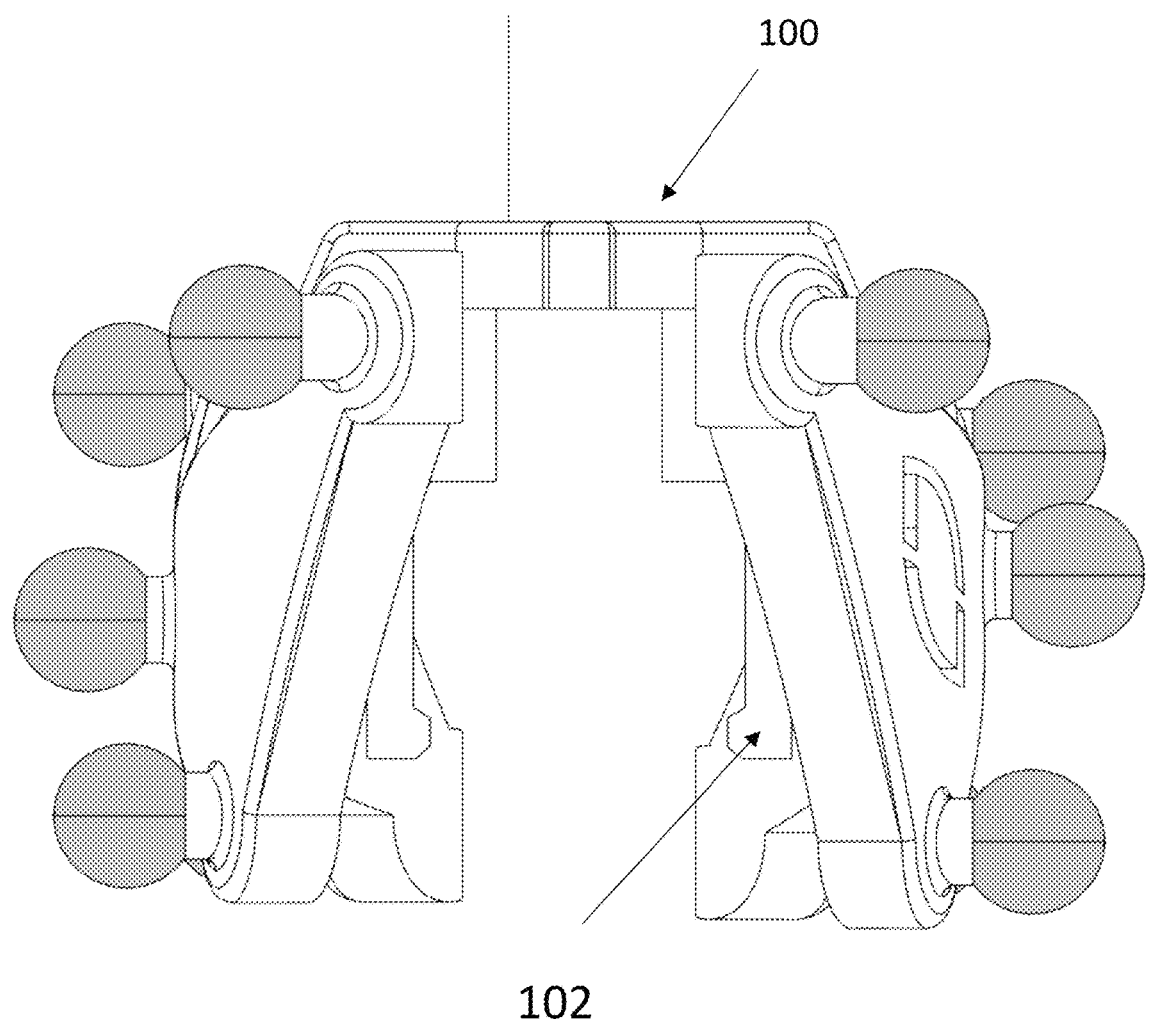
Figure 5G:
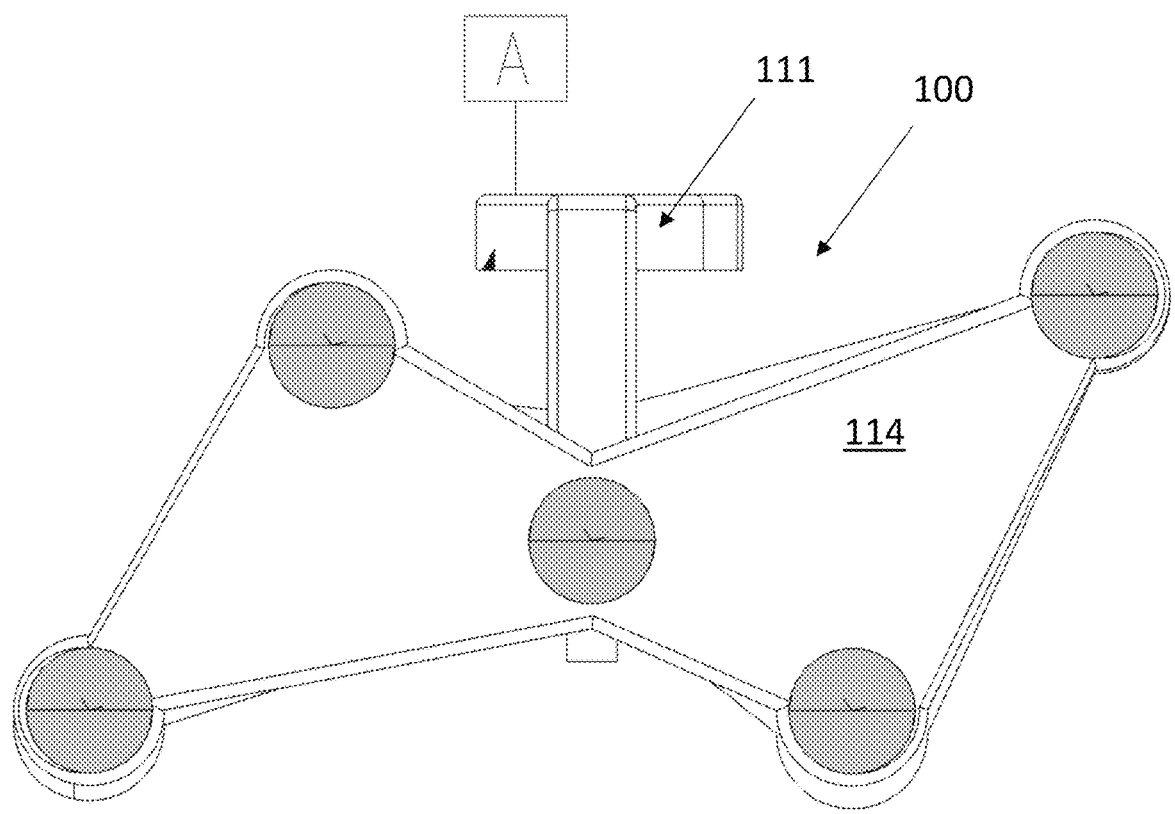

Non-limiting examples of the frame or array body can be cylindrical with a substantially circular cross-section (as shown in FIG. 3C), or an irregular cross section (as shown in FIG. 2C). The frame or array body may include through windows 110 therein extending from the outer surface to the inner cavity 106 of the array. The windows can allow visible detection of any additional medical instruments that goes through the cavity, for example, a k-wire. The frame or array body may be a ring shape as shown in FIG. 4A. The frame or array body may include two portion opposite to each other as shown in FIG. 5A. Such two portions may be connected by structural elements such as a bridge 111.

The cavity 106 may be extending entirely or partially from a proximal end 301 to a distal end 302 of the frame or body 103 of the array 100. The cavity 106 may enclose at least part of the medical instrument therewithin to reduce the increase to the overall size of the instrument and the array as well as facilitate coupling of the medical instrument to the tracking array.

Figure 2D:
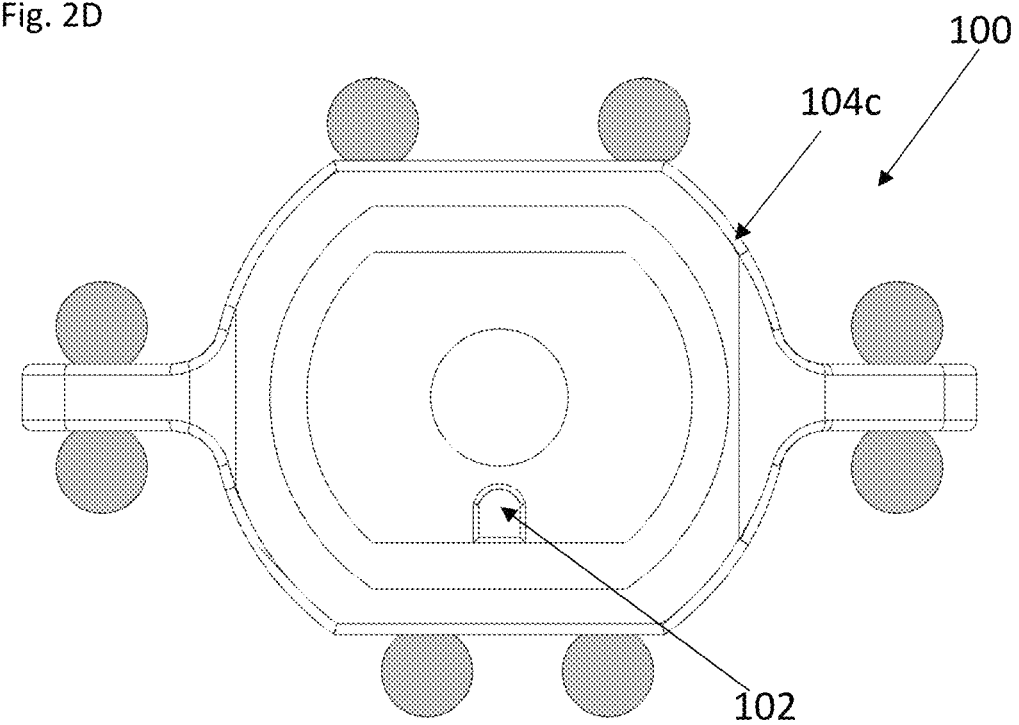
Figure 2E:
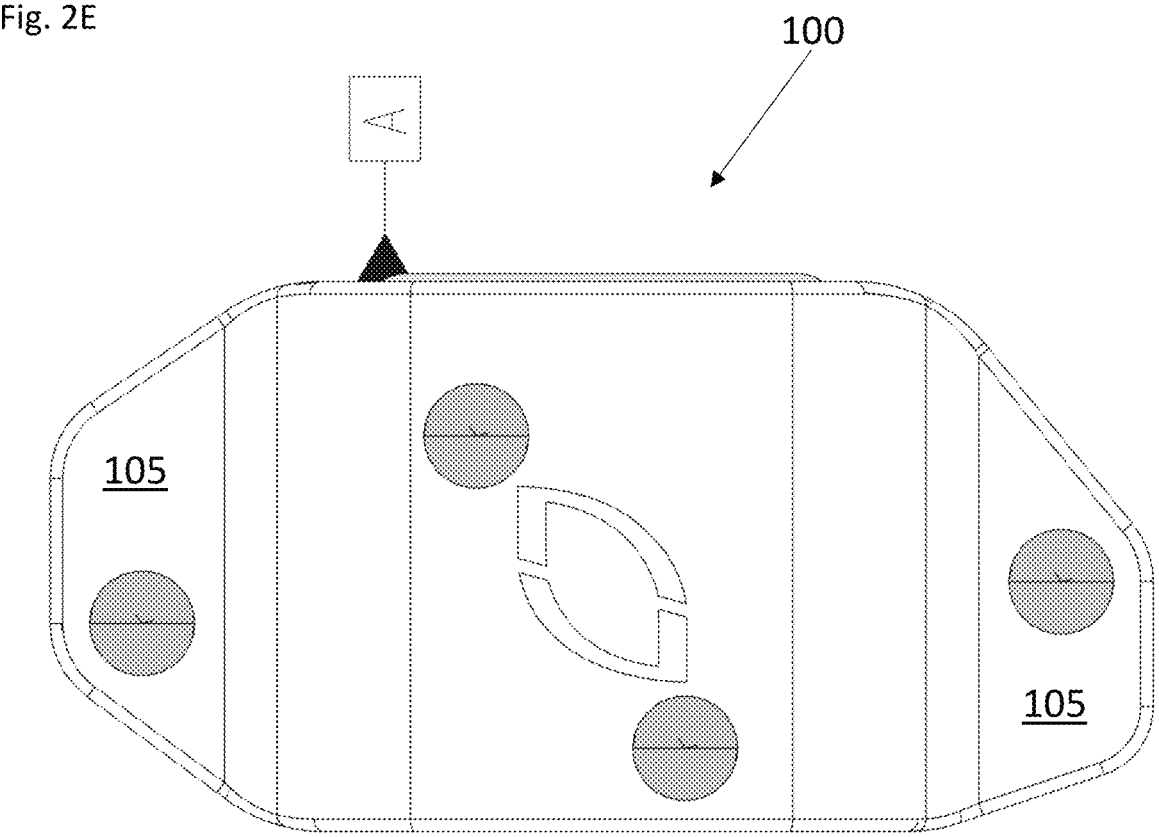
Figure 2F:
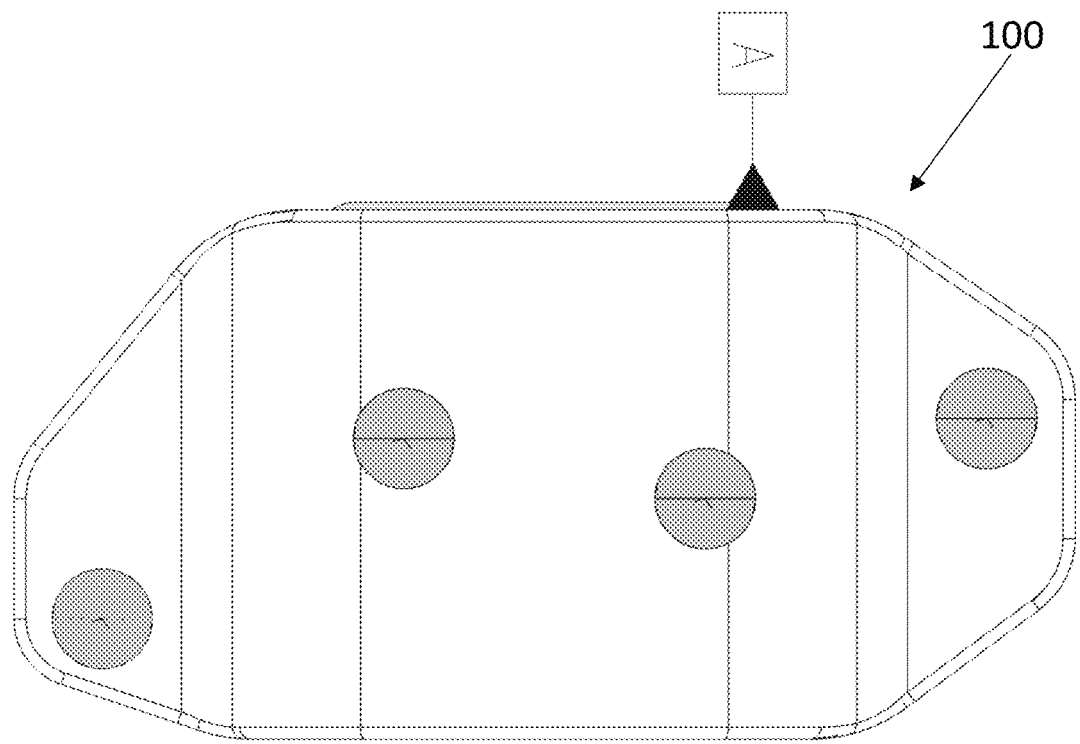
Figure 2G:
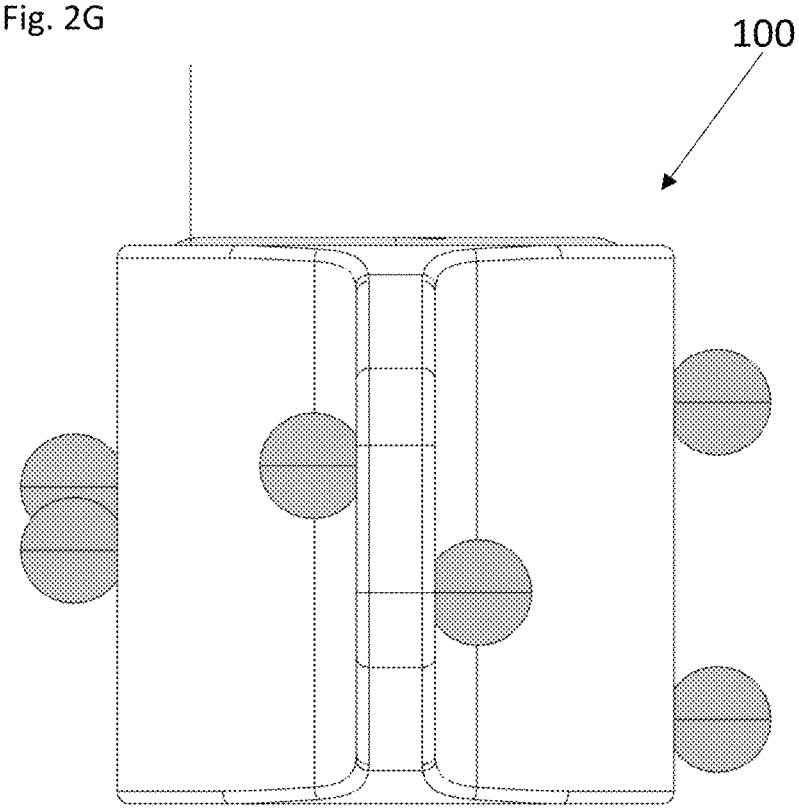
Figure 2H:
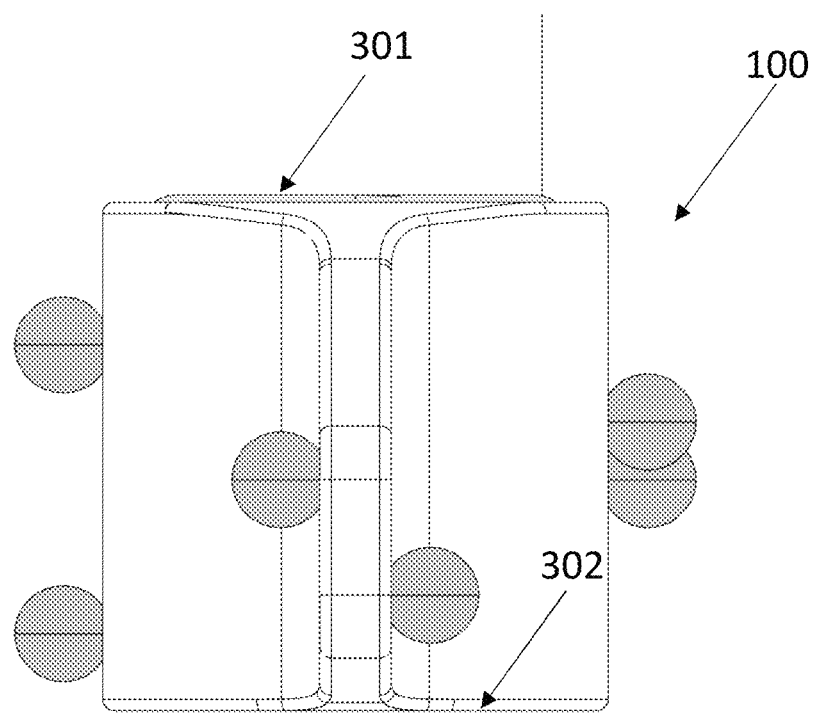

The array 100 may also include other structural elements attached to the frame or array body. As an example, the tracking array may include two side wings 105 attached to the elongate body 103, as shown in FIGS. 2A-2H. As another example, the tracking array may include a neck element 109 extending from inside of the cavity 106 to be distally outside of the elongate body 103, as shown in FIG. 3B. As yet another example, the tracking array includes a bridge 111 connected to the frame or array body 103, as shown in FIG. 5A, or a tail portion 107, as shown in FIG. 4A.

FIGS. 1A-1D show four different embodiments of the tracking array 100. A tracking array may be specifically designed in its three-dimensional (3D) geometric structure, size, and shape to be coupled to only one medical instrument 200. In some cases, a tracking array may be configured to couple to more than one medical instruments 200.

FIG. 1A shows an exemplary embodiment of the tracking array 100 that can be reversibly and securely attached to a medical instrument, in this case, a disc preparation instrument 200. Different views of the tracking array in FIG. 1A are shown in FIGS. 2A-2H. In this particular embodiment, the 3D structure of the tracking array includes an elongate body 103, a cavity located therewithin 106, and a first and a second side wing 105 attached to the elongate body. The cavity may allow insertion of the instrument partially or entirely through the cavity, and wherein the attachment feature 102 is located within the cavity. As shown in FIGS. 2E-2F, the first and second side wings 105 are not symmetrically positioned about a longitudinal axis along a proximal to distal direction (which is the vertical direction in FIGS. 2E-2F). The two side wings may be of different shape and size. In this embodiment, the outer surface includes a first flat surface 104a and a second flat surface 104b opposite to each other on the elongate body 103. Each of the first and second side wings includes a first and second flat surface 105a, 105b, opposite to each other. There may be a concave surface 104c connecting the first flat surface 104a on the elongate body to the first flat surface 105a of the first side wing. At least two tracking markers 101 are positioned on each of the first and second flat surfaces 104a, 104b on the elongate body and at least two tracking marker are positioned on each of the first and second side wings 105, and wherein no tracking marker is positioned on the concave surface 104c.

Figure 5H:
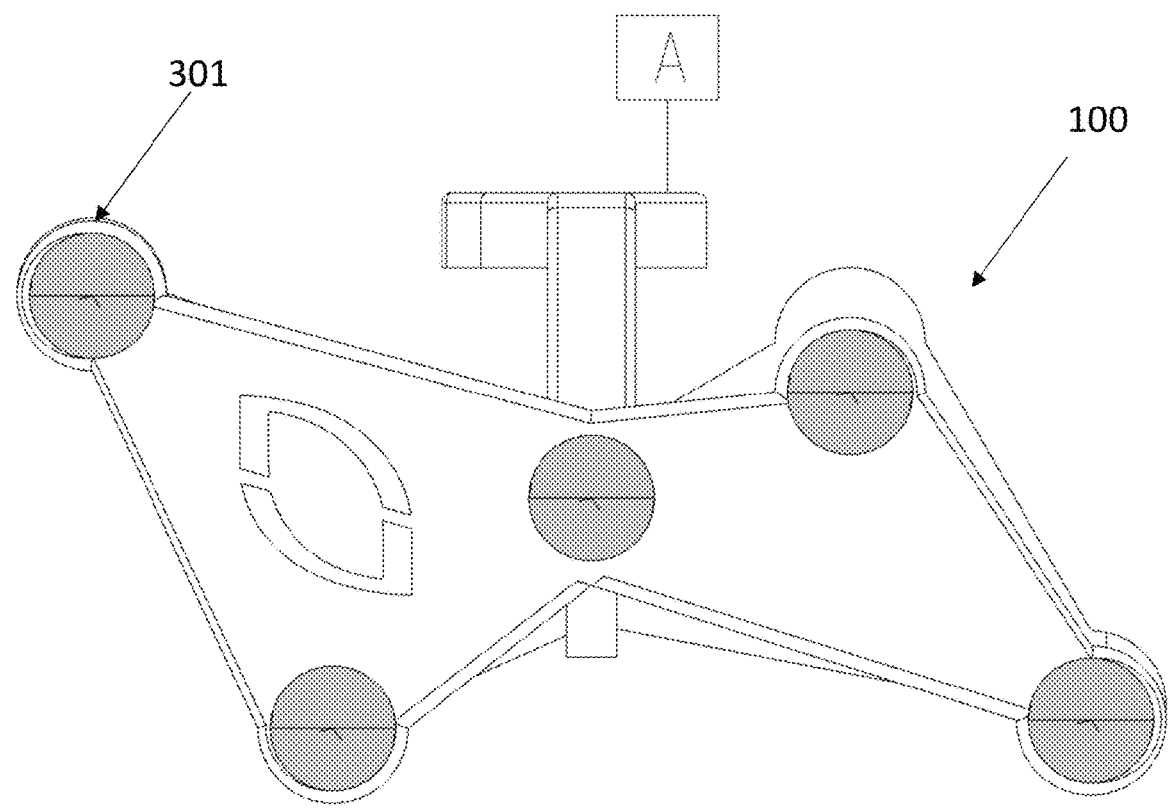

FIG. 1B shows another exemplary embodiment of the tracking array 100 that is attached to an implant inserter 200 near the proximal end of the inserter. Different views of the tracking array in FIG. 1B are shown in FIGS. 5A-5H. In this particular embodiment, the tracking array includes a first and a second concave wall 114 opposite to each other, and a bridge 111 connecting the concave walls at or near a center of the concave walls along a lateral direction (shown as the horizontal direction in FIG. 5C). The attachment feature 102 is positioned at a distal end of the bridge. The attachment feature in this particular embodiment, includes a pair of legs attached to a distal end of the bridge and extends more distally substantially along a longitudinal axis. Each leg may include a distal tip that extends inwardly toward the center of the the array body to ensure secure coupling to the complementary attachment feature on the instrument. A proximal end 301 of the first or second concave wall is more distal than a proximal end of the bridge as shown in FIG. 5H. The bridge 111 may not have any tracking marker thereon.

FIG. 1C shows another exemplary embodiment of the tracking array 100 that is attached to an initial dilator 200 at the proximal end of the dilator. In this particular case, the proximal end of the tracking array extends more proximally than the proximal end of the instrument. Different views of the tracking array in FIG. 1C are shown in FIGS. 3A-3H.

In this particular embodiment, the 3D structure comprises a cylindrical body 103 with two windows 110 opposite to each other, a cavity 106 located therewithin the cylindrical body, and a neck region 109 extending along a longitudinal axis beyond a distal edge of the cylindrical body 103. The attachment feature 102 is located within the neck region of the tracking array. The cylindrical body comprises a tip 112 extending distally from a distal end 302 of the cylindrical body, and a marker 113 at a proximal end 301 of the cylindrical body for assisting neuro-monitoring. The tracking array is configured such that, when the array is attached to the dilator, the cylindrical body is positioned so that the marker 113 is generally aligned with an electrode on the distal end of the dilator in order to provide a visual indicator to the surgeon of the location of the electrode when the distal end of the dilator is inside the body. This features helps the surgeon track the location of the nerves being stimulated by the electrode on the dilator during intra-operative neuro-monitoring. In some embodiments, more than one tracking markers and their position configuration allows a user to determine electrode stimulation directionality, e.g., all the tracking markers. In some embodiments, the relationship between all markers is what allows a user to determine the orientation of the stimulation direction. There can be a single marker that aligns with the stimulation direction, however, when this marker is not visible to the camera the orientation of the stimulation direction can still be calculated based on at least 1, 2, 3, 4, or even more other tracking markers that are available.

In some embodiments, there is a visual indication of the tracking array itself that guides the user to attach the tracking array in the proper orientation with the dilator. This orientation can be important to ensure the entirety of the marker configuration or a portion thereof aligns with the attachment feature e.g., flat on the dilator (which mates with the complementary attachment feature, e.g., complementary flat, in the tracking array). Without this attachment coupling, e.g., flat-to-flat mechanical coupling there may be no guarantee that the markers are displaying the true directionality of the dilator.

Figure 4G:
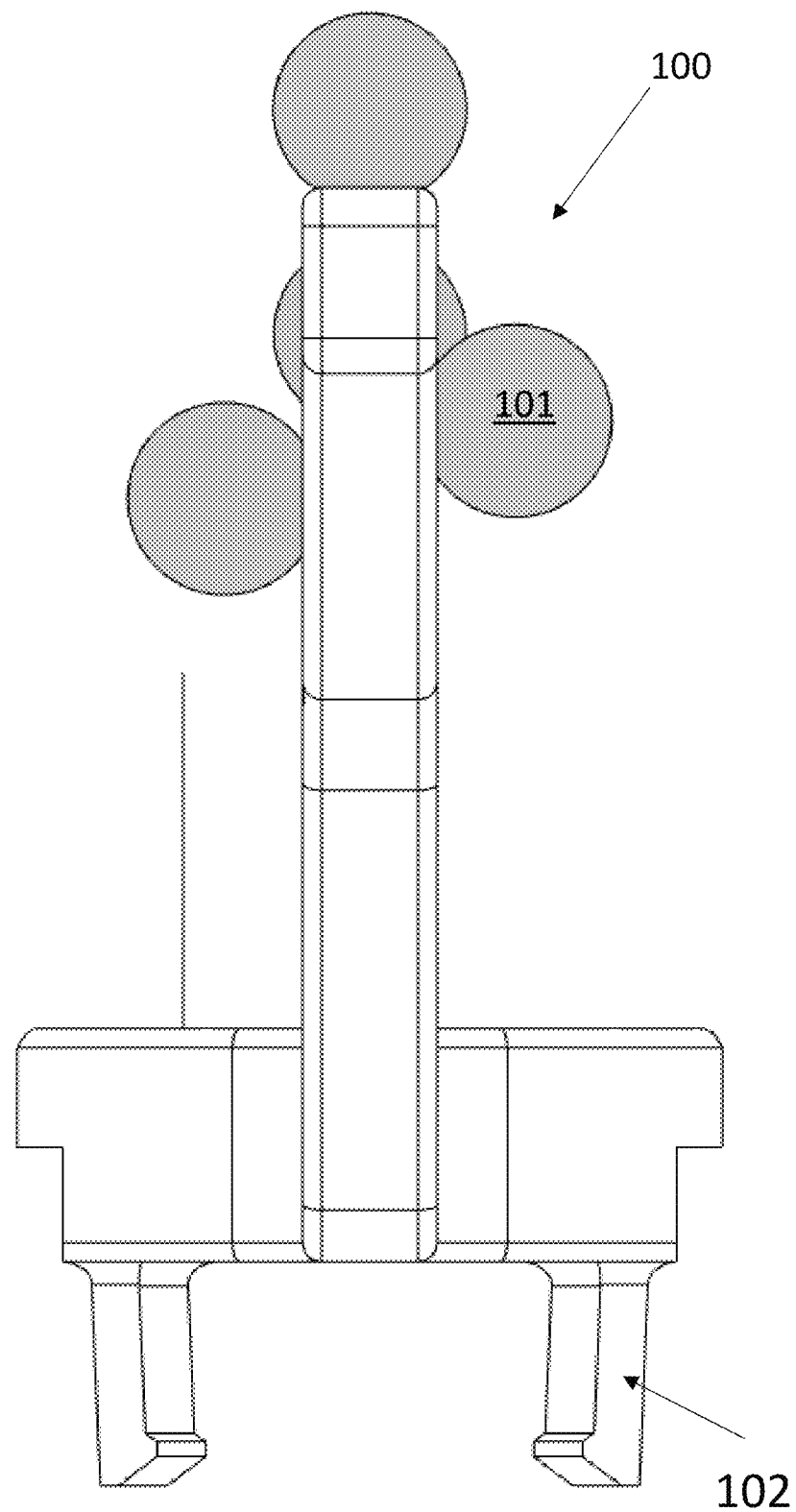
Figure 4H:
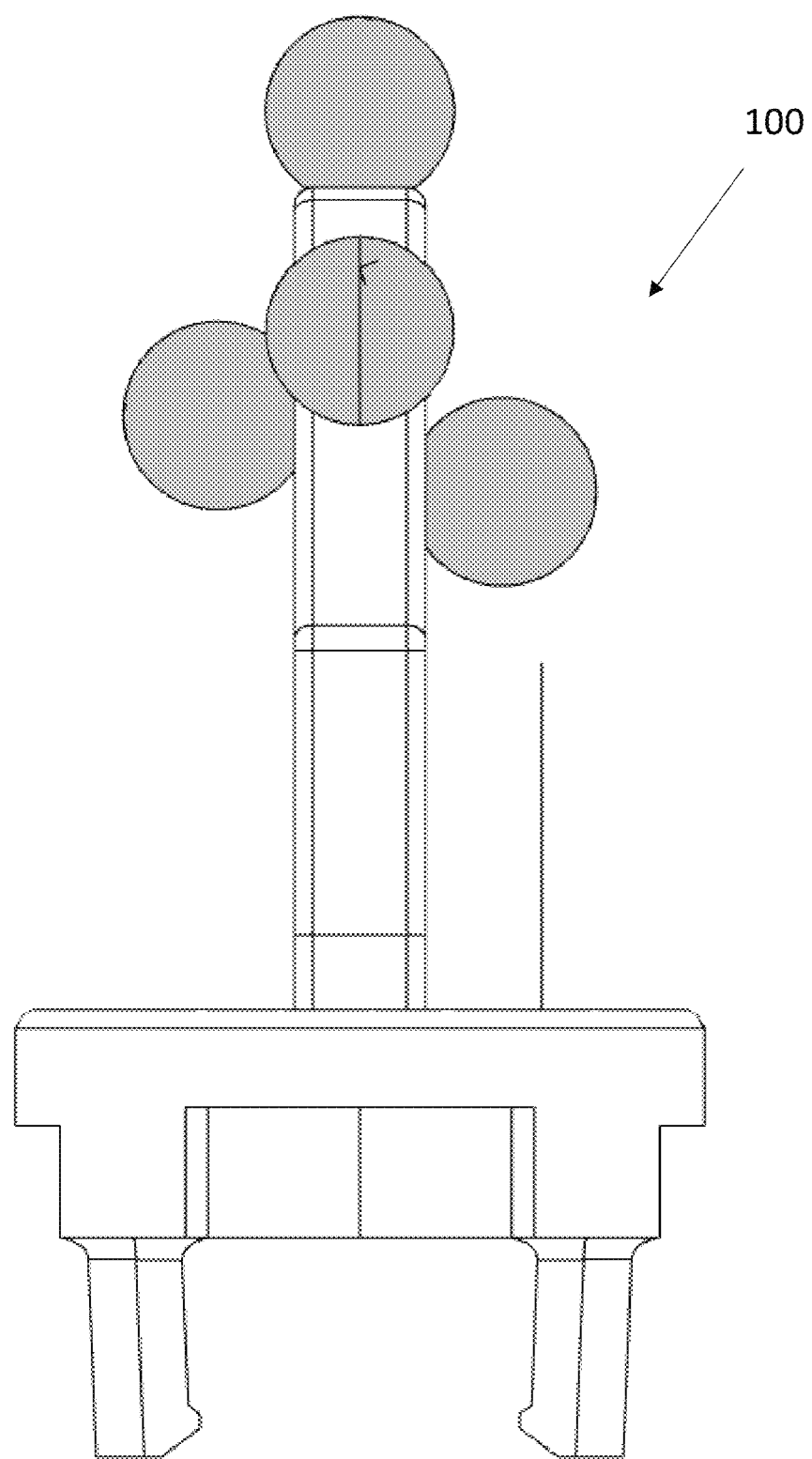

FIG. 1D shows another exemplary embodiment of the tracking array 100 that is attached to a retractor 200 at the proximal side of the retractor. Different views of the tracking array in FIG. 1D are shown in FIGS. 4A-4H. In this particular embodiments, the three-dimensional structure comprises a frame body 103 and a tail portion 107. The attachment feature 102 is positioned at a distal end of the body 103. The attachment feature in this particular embodiment, includes a pair of legs attached to a distal end of the frame or array body 102 and extends more distally substantially along a longitudinal axis. Each leg may include a distal tip that extends inwardly toward the center of the ring or the array body to ensure secure coupling to the complementary attachment feature on the instrument. The plurality of tracking markers may be positioned only at the tail portion 107 but not at the frame or array body. The tail portion includes a proximal surface 108a, a first and a second flat side surface 108c opposite to each other, and a distal surface 108b. No tracking marker is position on the distal surface 108b, and wherein a first tracking marker is placed on the first side wall 108c, and a second tracking marker is placed on the second side wall 108c. The first and second tracking markers are at different location along a proximal-to-distal direction as shown in FIGS. 4G-4H.

Attachment Features

In some embodiments, the tracking array 100 includes attachment features 102 that can securely engage with complementary attachment feature(s) 202 on the medical instrument thereby allowing safe, releasable, and secure coupling of the tracking array to the medical instrument. In some embodiments, the location, shape, and size of the attachment features of the tracking array, together with those of the complementary attachment feature on the medical instruments, are predetermined so as to advantageously prevent obstruction of the tracking markers by the surgeon and/or the patient once the tracking array is attached to the medical instrument.

The coupling between the attachment feature 102 and the complementary attachment feature 202 on the instruments 200 prevents relative movement of the tracking array with respect to the instrument once they are securely coupled to each other. In some embodiments, the tracking array is attached to the instrument near the proximal end 401 of the instrument.

The attachment feature may include one or more of: a prong or a leg, a groove, a ridge, an energy biasing element, e.g., a spring, and a thread. The prong or leg (FIGS. 4B and 5A) may extend inward toward a center of the array and may allow a snap-on coupling with the complementary groove or dent on the medical instrument. The attachment may occur between a male or female coupling with a peg or plug that can couple to a female or male coupling with a dent. As disclosed herein, the male coupling can be on one of the tracking array and the medical instrument, and the female coupling can be on the other of the tracking array and the medical instrument. Similarly, the peg or plug can be on one of the tracking array and the medical instrument, and the matching dent to the peg can be on the other of the tracking array and the medical instrument. The attachment feature may enable a slide-on coupling with the complementary attachment feature as shown in FIGS. 1A and 2D.

Tracking Markers

In some embodiments, the tracking array includes more than one tracking markers. The tracking markers can be located only on the outer surface of the tracking array. The relative position of two or more tracking markers, e.g., immediately adjacent markers, can be specifically determined so that each marker visible to the image capturing device can be uniquely identified. As such, the orientation and/or position of the medical instrument can be accurately determined based on the tracking information of the more than one markers.

In some embodiments, the relative position of one or more tracking markers to a reference point on the frame of the array (e.g., distal edge of the tracking array) is specifically determined so that, at a particular time point, at least 3 markers are visible and/or non-overlapping to the image capturing device no matter what the relative orientation of the instrument is in regard to the camera.

In some embodiments, the relative position of two or more tracking markers and/or the relative position of the marker(s) to the frame of the tracking array are pre-determined so that there are at least three markers visible and/or non-overlapping to the image capturing device no matter how the instrument is moved in 3D by a user during a medical procedure relative to the image capturing device. In some embodiments, a minimum number of 3 tracking markers are always detectable to the image capturing device with an arbitrary movement of the tracking array and the medical instrument relative to the image capturing device. The movement can be translation and/or rotation in 3D. In some embodiments, the tracking arrays herein are 360° arrays that enable detection of the instrument with any orientation or location in or near the patient. The plurality of tracking markers can be positioned on the outer surface so that at least 4, 5, 6, 7, 8, 9, or 10 of the plurality of tracking markers are visible to the image capturing device at a specific time point when the tracking array is rotated to an arbitrary rotation angle in three-dimension and/or moved relative to the image capturing device.

Since any two or three tracking markers are positioned uniquely relative to each other and/or to a reference point on the tracking array, when 3 tracking markers are detected, the surgical navigation system can figure out what these 3 tracking markers are and where they are located on the tracking array thereby generating accurate information of the location and orientation of the medical instrument.

In some embodiments, each tracking array has a unique arrangement of tracking markers when compared with other tracking arrays, so that when the surgical navigation system and/or the digital processing device recognizes a particular arrangement, the surgical navigation system can know which tracking array and which instrument is being tracked or navigated. As such, the surgical navigation system can render the correct instrument on the digital display for navigation purpose. In some embodiments, only the tracking marker are visible to the image capturing device so that such recognition cannot be performed using the different shapes of the tracking array but need to be the unique arrangement of the tracking markers. In some embodiments, the unique arrangement of the tracking markers includes relative position of a marker to another marker or to a reference point. The unique arrangement of the tracking markers may also include size, shape or any other parameters of the tracking marker. As an example, the image capturing device is able to capture 8 tracking markers at the same time, and they are evenly distributed along a circumference and such unique arrangement indicates that the navigated instrument is the dilator.

In some embodiments, the tracking markers include a reflective surface or a reflective coating that reflects light in a specific electromagnetic frequency range. In some embodiments, the tracking markers are spherical or sufficiently spherical. In some embodiments, the markers are identical in size and shape. In other embodiments, the markers can be of 3D shapes other than sphere and/or of sizes that are not identical. In some embodiments, two or more of the plurality of tracking markers comprise an identical shape, size, or both. In some embodiments, all of the plurality of tracking markers comprises an identical shape, size or both.

In some embodiments, the plurality of tracking markers is positioned on the tracking array so that all the of the plurality of tracking markers are non-overlapping and visible to the image capturing device when viewed along a proximal-to-distal direction, for example, as shown in FIGS. 2C, 3C, 4C, and 5D.

In some embodiments, the plurality of tracking markers is all at different distances to a reference point (e.g., the proximal edge or distal edge) on the frame or array body, as shown in FIGS. 2G-2H, and FIGS. 3G-3H.

In some embodiments, at least part of the frame or array body is curved so that the tracking markers do not lie in a single flat two-dimensional plane, but instead, any two or three tracking markers can be in a two-dimensional plane different from a two-dimensional plane that another two or three tracking markers belong.

In some embodiments, there is no tracking marker within the cavity 106, on the neck 109, bridge 111, or body (FIG. 4A) of the tracking array.

In some embodiment, "visible" herein indicates full visibility—the perimeter or outer contour, and the area therewithin a tracking marker are completely free of obstruction by any other tracking markers. In some embodiments, "visible" herein indicates partial visibility—at least a part of the perimeter or outer contour or at least a part of the area therewithin a tracking marker are not obstruction by any other tracking markers.

In some embodiments, "non-overlapping" herein indicates not any obstruction or partial obstruction of a tracking marker by any other tracking markers.

In some embodiments, the tracking marker includes geometric core, e.g., a sphere, made of biocompatible material, and a reflective or otherwise visible coating or film thereon to reflect light or otherwise generate detectable signal to the image capturing device. In some embodiments, the tracking markers may be a patch that is on the outer surface of the tracking array. The patch may be 2D and lay flat on the outer surface. The patch may be 3D with a height above the outer surface. In some embodiments, the tracking marker may be in the shape of a disco mirror ball or any other 3D geometry with multiple reflective surfaces.

Medical Instruments

In some embodiments, the tracking array can be attached to a medical instrument. More particularly, the tracking array disclosed herein can be attached to medical instruments for performing spinal surgeries. In some embodiments, the tracking array may be customized to be attached to a specific instrument. In some embodiments, the medical instrument can be any medical instrument with a proximal portion that is sized and shaped to be compatible with the tracking array. For example, the tracking array shown in FIG. 1A can be attached to a variety of disc preparation instruments for removal of the intervertebral disc or preparing the disc space for further operation. Such medical instruments can also be other instruments with a handle that has a proximal portion compatible to the cavity of the tracking array and the attachment feature in the tracking array.

In some embodiments, the medical instruments can be disc preparation tools or instruments, retractors, implant inserters, and dilators.

The medical procedure herein is equivalent to a medical operation, a surgical procedure, a surgical operation, and a surgery. The medical procedure can be a minimally invasive surgery. The medical procedure can include a spinal surgery. The medical procedure can include one or more of spinal fusion, decompression, alignment, disc replacement, corpectomy, and stabilization. The medical procedure can include one or more of posterior lumbar interbody fusion (PLIF), transforaminal lumbar interbody fusion (TLIF), anterior lumbar interbody fusion (ALIF), and extreme lateral interbody fusion (XLIF).

Complementary Attachment Features

In some embodiments, the medical instrument herein may include one or more complementary attachment features 202 that couples to the attachment feature(s) 102 on the tracking array thereby allowing safe, releasable, and secure coupling of the tracking array to the medical instrument.

The coupling between the attachment feature and the complementary attachment feature on the instruments prevents relative movement of the tracking array with respect to the instrument once they are securely coupled to each other. In some embodiments, complementary attachment feature is positioned relatively closer to the proximal end of the medical instrument than the distal end of the instrument. In some embodiments, the complementary attachment feature is at or near the proximal end of the medical instrument.

The complementary attachment feature may include any feature that is complementary to the specific attachment feature of the tracking array. Non-limiting examples of the complementary attachment feature include one or more of: a prong or a leg, a groove, a dent (as shown in FIGS. 7A-7B), a ridge, an energy biasing element, and a thread.

In some embodiments, the complementary attachment feature may be part of the medical instrument. The complementary attachment feature may be added to a traditional medical instrument, for example, a sleeve with complementary attachment feature that slides on to a handle of the traditional medical instruments and locks thereon.

In some embodiments, the complementary attachment features and/or the attachment feature are positioned so that the attachment of the tracking array to the medical instrument causes minimal if any interference to the operation of the medical instrument. In some embodiments, the complementary attachment features and/or the attachment feature are positioned so that when attached, at least 3 or more tracking markers are not obstructed by the surgeon or the patient's anatomy or otherwise other objects that obstruct or interferes the communication of optical signal from the tracking marker to the image capturing device.

Figure 7A:
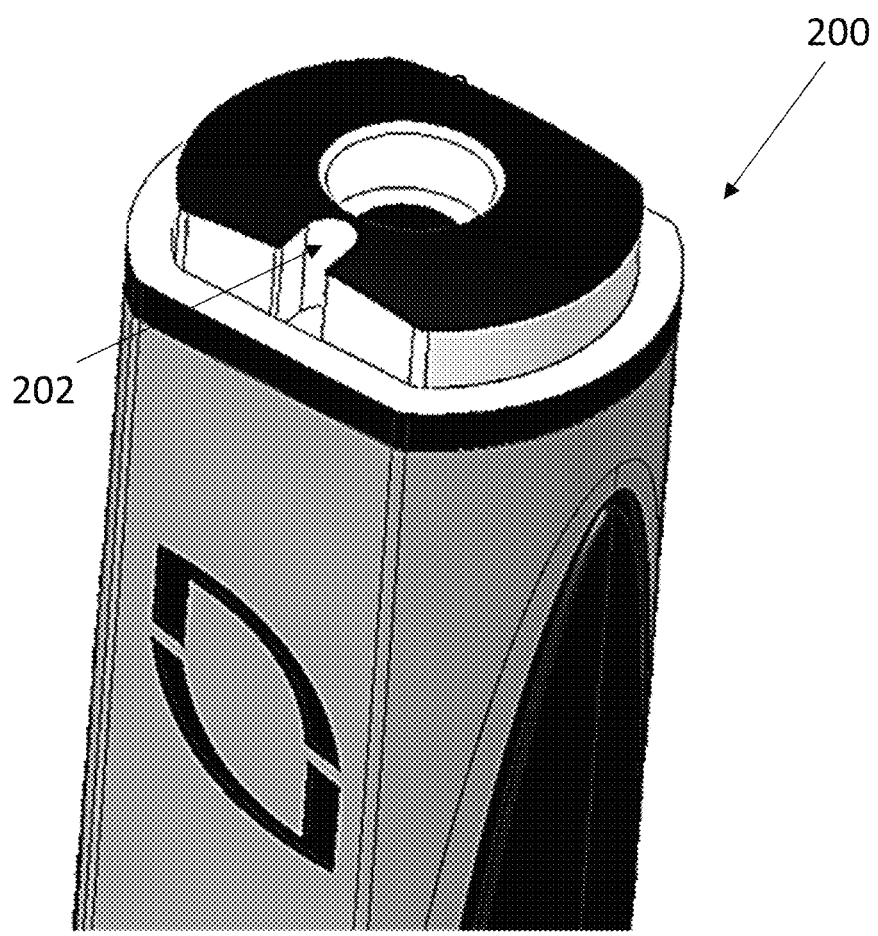
FIGS. 7A-7C show different views of the handle of the disc preparation tool in FIG. 1A.
Figure 7B:
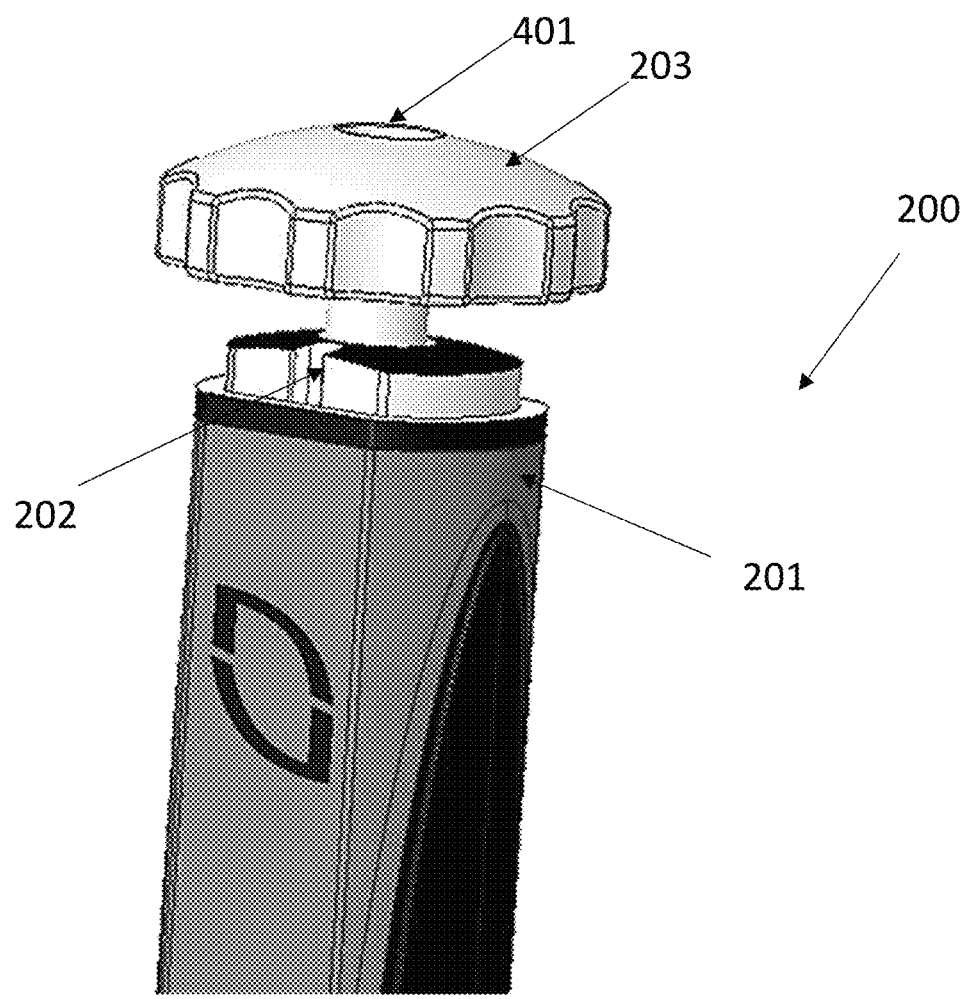
Figure 7C:
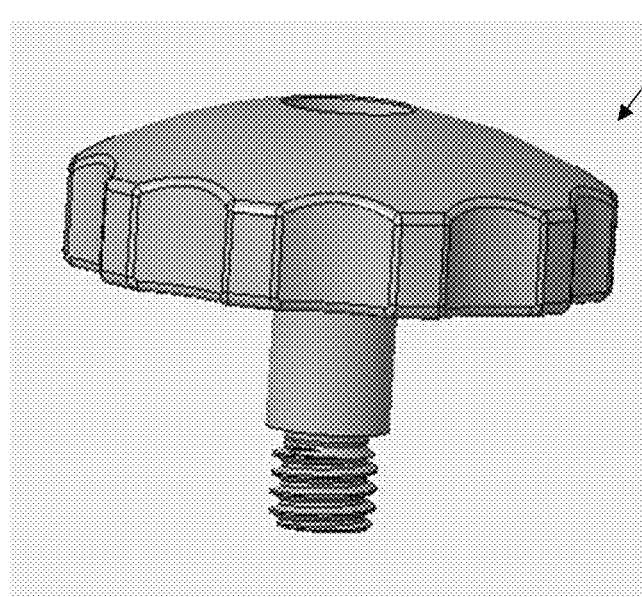

FIGS. 7A-7C show perspective views of the disc preparation tool 200 in FIG. 1A. The complementary attachment feature includes a matching dent 202 to receive the plug 102 in FIG. 2D. The matching dent extends longitudinally with a predetermined length and includes a curved surface connecting to two flat side surfaces. The cross-section perpendicular to the proximal-distal direction is proximally a U shape. FIG. 7B shows the medical instrument without attachment of a tracking array between the handle 201 and the end cap 203. The end cap 202 can be used to secure the array to the disc prep instrument 202 via the threading at the distal portion thereof, and also protect the tracking array from damages caused by operations of the disc preparation tool by the surgeon.

Figure 8A:
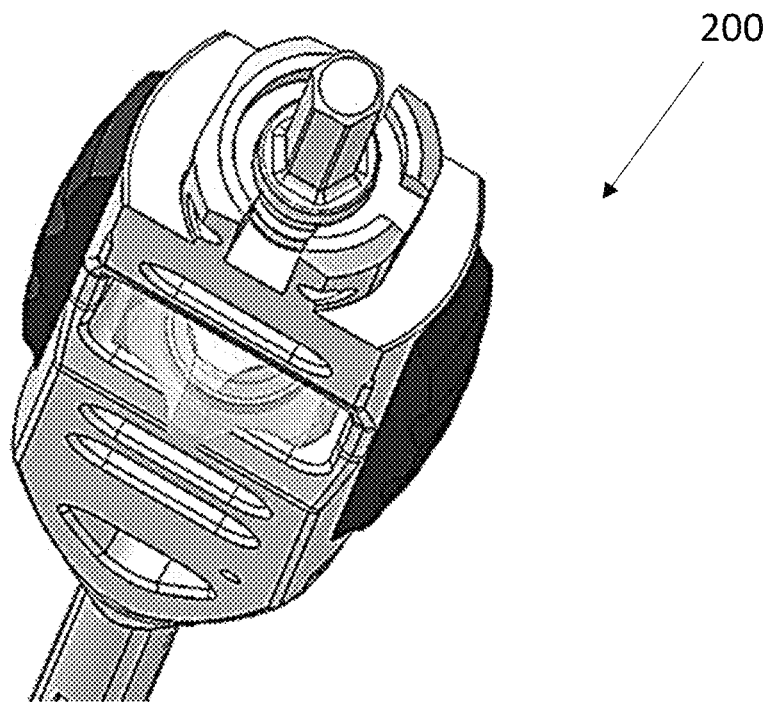
FIGS. 8A-8B show different views of the proximal portion of the implant inserter in FIG. 1B.
Figure 8B:
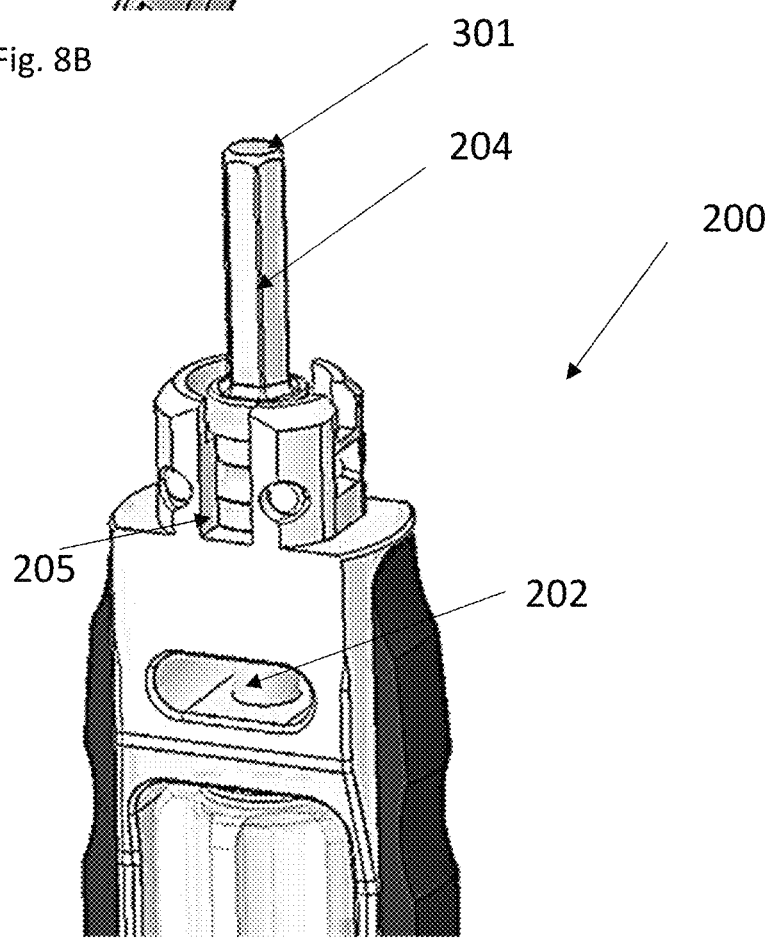
Figure 9:
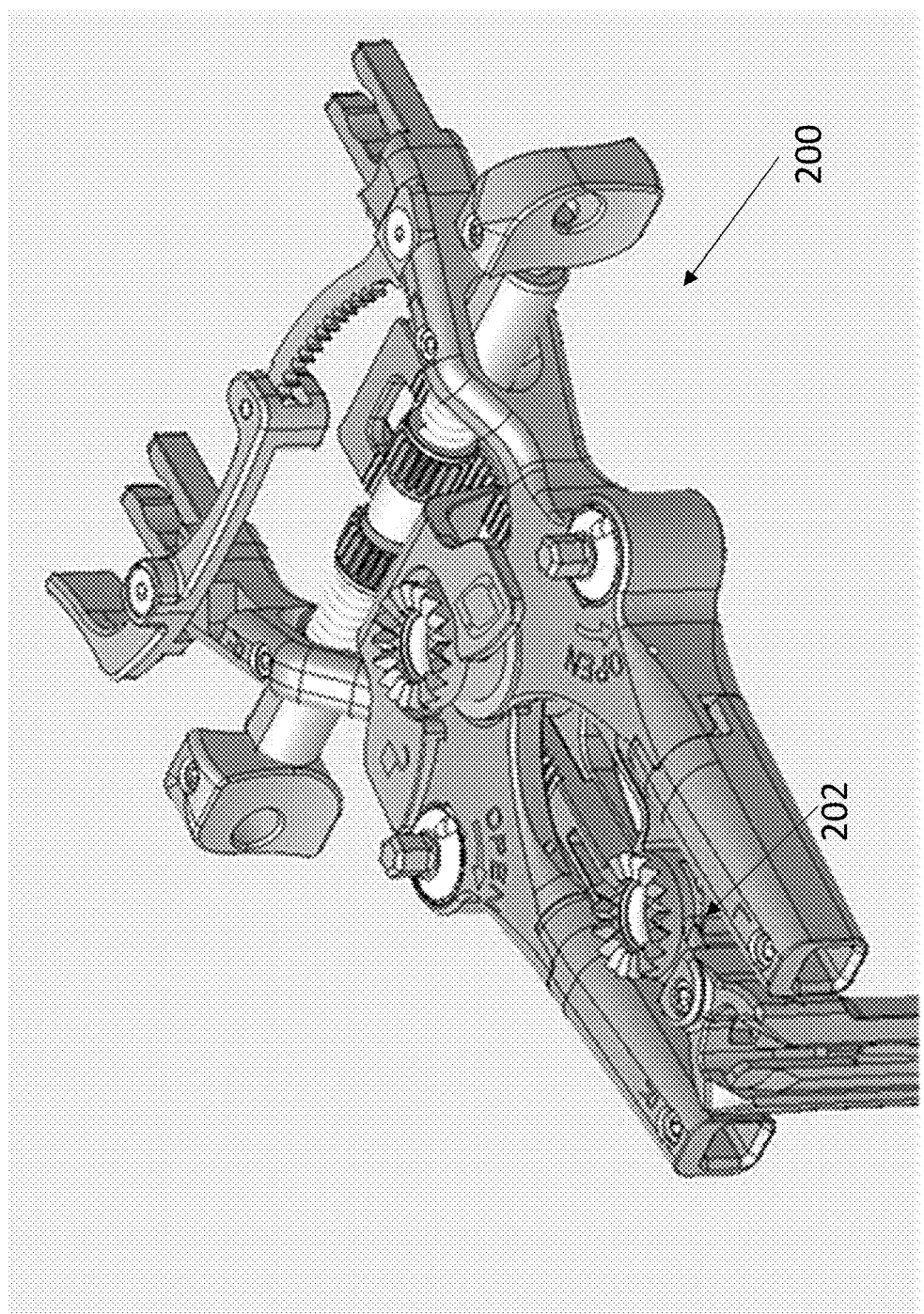
FIG. 9 shows a perspective view of the retractor in FIG. 1D.

FIGS. 8A-8B and 9 show the complementary attachment feature 202 on the implant inserter and retractor, respectively. In these particular embodiments, the complementary attachment feature includes a groove that can receive the leg(s) on the tracking array thereby enabling snap-on coupling of the tracking array and the instrument. In addition, the inserter can include a central core 204 that goes through an opening located on the bridge 111 of the tracking array, and additional cut-outs 205 that accommodate the proximal portion of the legs 102 of the tracking array.

Figure 10A:
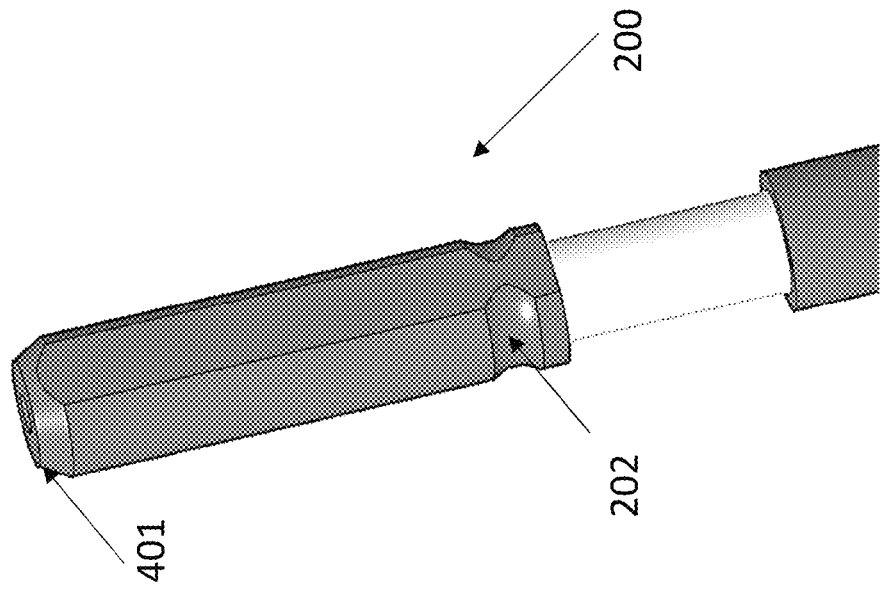
FIGS. 10A-10B show the perspective views of the dilator shown in FIG. 1C.
Figure 10B:
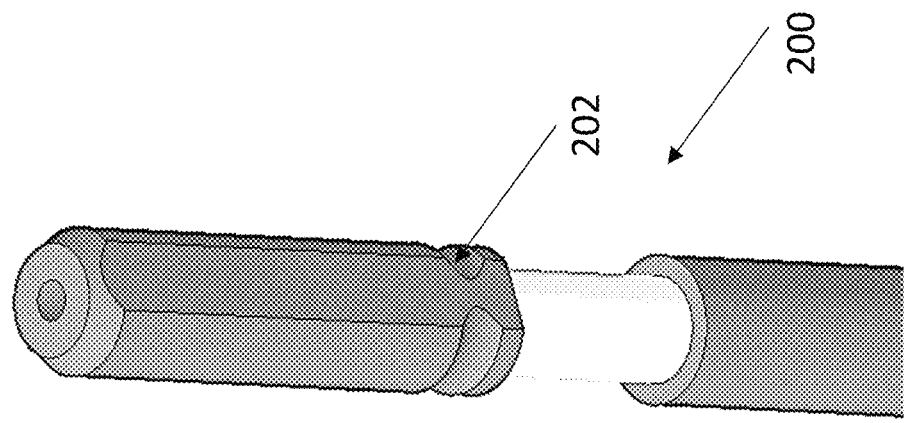

FIGS. 10A-10B show the complementary attachment feature 202 near a proximal end 401 of the dilator. The complementary attachment feature can include a groove 202 that can receive the ridge(s) 102 on the inside of the neck of the tracking array thereby enabling snap-on coupling of the tracking array and the instrument. In addition, the dilator goes through an opening located the neck 109 of the tracking array at least partly to ensure proper coupling of the array to the dilator.

Image Capturing Devices

The systems, methods, and apparatuses disclosed herein include an image capturing device. The image capturing device can be any device that is capable of capturing information of the tracking markers. The image capture device can utilize one or more imaging modalities. In some embodiments, the image capturing device can include a camera. The camera may utilize visible light, infrared light, other electro-magnetic waves in the spectrum.

In some embodiments, the image capturing device is in communication with the surgical navigation system herein for data communication, or operational control of the image capturing device. Such communication may be unidirectional or bidirectional.

In some embodiments, the image capturing device includes an imaging sensor or a lens for detecting signal, e.g., infrared light. In some embodiments, the image capturing device includes one or more software modules for generating images using signal detected at the imaging sensor. In some embodiments, the image capturing device includes a communication module so that it communicates data to the system, the digital processing device, a digital display, or any other devices disclosed herein.

In some embodiments, the image capturing device includes one or more camera or lenses. In some embodiments, the image capturing device includes a camera having at least two lenses at a fixed position relative to each other. In some embodiments, each lens detects a two-dimensional image and at least two two-dimensional images can be used to generate 3D information of the tracking markers. In some embodiments, the camera or lens detects reflective light from the tracking markers. The reflective light may be infrared light.

In some embodiments, the image capturing device includes a light source that transmits light to the tracking markers.

In some embodiments, the image capturing device can be free moving in 3D relative to the patient or the tracking array. The movement can include translation and/or rotation while the relative position of the two lenses within the device remains unaltered.

Navigation Systems

In some embodiments, disclosed herein is a system for surgical navigation. The system herein can be a surgical navigation system. The system can include a tracking array having a plurality of tracking markers arranged on an 3D outer surface of the tracking array; an attachment feature configured to releasably and securely attach the tracking array to a medical instrument; one or more image capturing device, e.g., camera(s), for tracking at least three of the plurality of tracking markers simultaneously; and a surgical navigation system that communicates with the image capturing device and generates surgical navigation information based on the tracking of the plurality of tracking markers.

In some embodiments, the surgical navigation system described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 6:
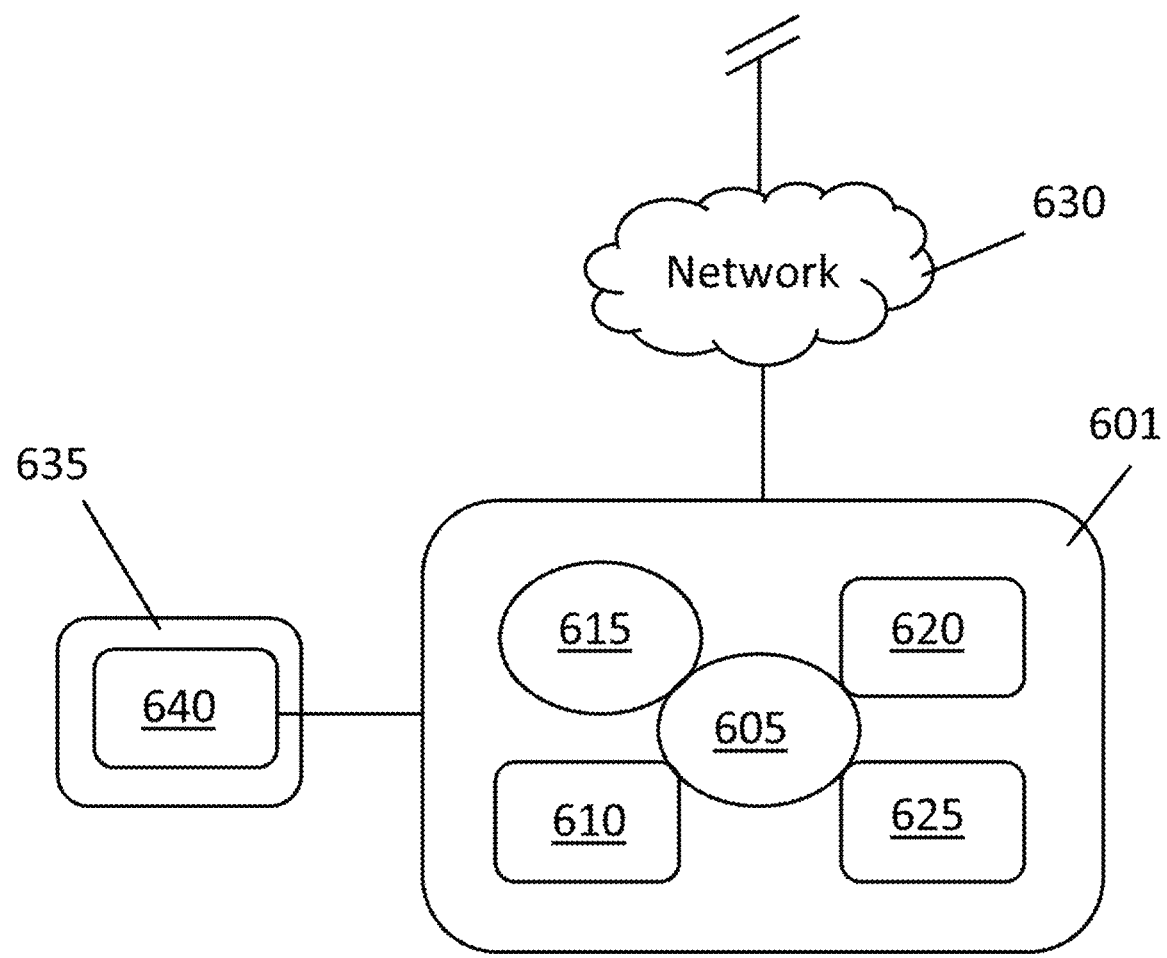
FIG. 6 shows an exemplary embodiment of the digital processing device of the surgical navigation system disclosed herein.

Referring to FIG. 6, in a particular embodiment, an exemplary digital processing device 601 is programmed or otherwise configured to estimate visual acuity of a subject. The device 601 can regulate various aspects of the algorithms and the method steps of the present disclosure. In this embodiment, the digital processing device 601 includes a central processing unit (CPU, also "processor" and "computer processor" herein) 605, which can be a single core or multi core processor, or a plurality of processors for parallel processing. The digital processing device 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The digital processing device 601 can be operatively coupled to a computer network ("network") 660 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the device 601, can implement a peer-to-peer network, which may enable devices coupled to the device 601 to behave as a client or a server.

Continuing to refer to FIG. 6, the CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and write back. The CPU 605 can be part of a circuit, such as an integrated circuit. One or more other components of the device 601 can be included in the circuit. In some embodiments, the circuit is an application specific integrated circuit (ASIC) or a field programmable gate array (FPGA).

Continuing to refer to FIG. 6, the storage unit 615 can store files, such as drivers, libraries and saved programs. The storage unit 615 can store user data, e.g., user preferences and user programs. The digital processing device 601 in some cases can include one or more additional data storage units that are external, such as located on a remote server that is in communication through an intranet or the Internet.

Continuing to refer to FIG. 6, the digital processing device 601 can communicate with one or more remote computer systems through the network 630. For instance, the device 601 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 601, such as, for example, on the memory 610 or electronic storage unit 615. The machine executable or machine readable code can be provided in the form of software. During use, the code can be executed by the processor 605. In some embodiments, the code can be retrieved from the storage unit 615 and stored on the memory 610 for ready access by the processor 605. In some situations, the electronic storage unit 615 can be precluded, and machine-executable instructions are stored on memory 610.

Non-Transitory Computer Readable Storage Medium

In some embodiments, the systems and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some embodiments, the program and instructions are permanently, substantially permanently, semi-permanently, or non-transitorily encoded on the media.

Computer Program

In some embodiments, the systems and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Software Modules

In some embodiments, the systems and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Although certain embodiments and examples are provided in the foregoing description, the inventive subject matter extends beyond the specifically disclosed embodiments to other alternative embodiments and/or uses, and to modifications and equivalents thereof. Thus, the scope of the claims appended hereto is not limited by any of the particular embodiments described herein. For example, in any method disclosed herein, the operations may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the systems, and/or devices described herein may be embodied as integrated components or as separate components.

Method Steps

In some embodiments, disclosed herein is a method for surgical navigation. The method may include one or more method steps or operations disclosed herein but not necessarily in the order that the steps or operations are disclosed herein. One or more method steps or operations disclosed herein can be performed in real-time or near real-time so that it advantageous facilitate continuous guidance of the surgical procedure.

One or more steps can be performed so that no perceivable delay can be detected by the technician, surgeon, or otherwise user of the systems. One or more steps can be performed so that no perceivable delay exists in performing the medical procedure.

In some embodiments, real-time performance disclosed herein include a very small delay of less than 1 second, 0.8 seconds, 0.6 seconds, 0.5 seconds, 0.4 seconds, 0.3 seconds, 0.2 seconds, 0.1 seconds, 0.08 seconds, 0.06 seconds, 0.05 seconds, 0.02 seconds, or 0.01 seconds. In some embodiments, real-time performance disclosed herein includes a very small delay of less than about 1 second, 0.8 seconds, 0.6 seconds, 0.5 seconds, 0.4 seconds, 0.3 seconds, 0.2 seconds, 0.1 seconds, 0.08 seconds, 0.06 seconds, 0.05 seconds, 0.02 seconds, or 0.01 seconds. The time delay herein can be the time duration from the onset of a step to the end of the same step, or any subsequent step(s).

As a non-limiting example, one or more 3D images of the medical instrument is presented to a surgeon on a digital display in the operating room, and such presentation of one or more 3D image of the instrument is updated in near real-time (e.g., in less than about 0.1 seconds) when the surgeon moves the instrument.

In some embodiments, the methods disclosed herein include releasably attaching a tracking array to a medical instrument by engaging the attachment feature of the tracking array with the complementary attachment feature of the medical instrument. The methods may also include tracking the tracking array, by an image capturing device, optionally, during a medical procedure thereby generating tracking information of the tracking array. Such tracking information can be communicated by the image capturing device to the navigation system; and such tracking information can be used to generate one or more images of the medical instrument, the tracking array, or both. Such images can then be displayed by a digital display, to a medical professional for assisting an ongoing or a forthcoming medical procedure.

In some embodiments, disclosed herein is a method for surgical navigation. The method can include providing a tracking array with an attachment feature. The method can optionally include providing a medical instrument with a complementary attachment feature that can couple to the attachment feature. The method can alternatively include providing a complementary attachment feature that can be attached to a traditional medical instrument. The method may include allowing a user to releasably attach the tracking array to the medical instrument by engaging the attachment feature of the tracking array with the complementary attachment feature of the medical instrument so that there is no relative movement between the tracking array and the medical instrument when coupled to each other. The method can then include allowing a user to track the tracking array, by an image capturing device, when the tracking array and the medical instrument combo moves optionally during a medical procedure thereby generating tracking information. Such tracking information can be communicated from the image capturing device to a digital processing device to present images of the medical instrument to the user.

All publications, patents, and patent applications mentioned in this specification are herein incorporated by reference to the same extent as if each individual publication, patent, or patent application was specifically and individually indicated to be incorporated by reference.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "and," "or" herein is intended to encompass "and/or" unless otherwise stated. As used in this specification and the claims, unless otherwise stated, the term "about," "substantially," and "approximately" can refers to variations of less than or equal to +/−1%, +/−2%, +/−3%, +/−4%, +/−5%, +/−6%, +/−7%, +/−8%, +/−9%, or +/−10% depending on the embodiment. As used in this specification and the claims, unless otherwise stated, the term "about," and "approximately" can refers to variations of less than or equal to +/−11%, +/−12%, +/−14%, +/−15%, or +/−20% depending on the embodiment. As a non-limiting example, about 100 meters can represent a range of 95 meters to 105 meters or 90 meters to 110 meters depending on the embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A tracking array for surgical navigation, the tracking array comprising:
   a three-dimensional structure having:
      an elongate body with a cavity located therewithin,
      an outer surface including a first flat surface and a second flat surface opposite to each other on the elongate body,
      a first and a second side wing attached to the elongate body and not symmetrically positioned about a longitudinal axis along a proximal to distal direction, each of the first and second side wings including a first and second flat surface opposite to each other, and
      a concave surface connecting the first flat surface on the elongate body to the first flat surface of the first side wing;
   a plurality of tracking markers arranged on the outer surface of the tracking array, the plurality of tracking markers configured to be detectable by an image capturing device; and
   an attachment feature configured to releasably and securely attach the tracking array to an object.

2. The tracking array of claim 1, wherein at least a portion of the outer surface is curved.

3. The tracking array of claim 1, wherein the image capturing device comprises one or more of an optical camera, and an infrared light camera.

4. The tracking array of claim 1, wherein one or more of the plurality of tracking markers comprise a spherical surface.

5. The tracking array of claim 1, wherein one or more of the plurality of tracking markers are configured to reflect an optical signal which is captured by the image capturing device.

6. The tracking array of claim 1, wherein two or more of the plurality of tracking markers comprise an identical shape, size, or both.

7. The tracking array of claim 1, wherein the plurality of tracking markers is positioned on the outer surf ace so that at least 3 or 4 of the plurality of tracking markers are visible simultaneously to the image capturing device when the tracking array is rotated with an arbitrary rotation angle in three-dimension.

8. The tracking array of claim 1, wherein the plurality of tracking markers is positioned so that all of the plurality of tracking markers are non-overlapping and visible to the image capturing device when viewed along a proximal-to-distal direction.

9. The tracking array of claim 1, wherein at least two tracking markers are positioned on each of the first and second flat surface on the elongate body and at least two tracking markers are positioned on each of the first and second side wings, and wherein no tracking marker is positioned on the concave surface.

* * * * *